(12) United States Patent
Quart et al.

(10) Patent No.: US 7,556,831 B2
(45) Date of Patent: Jul. 7, 2009

(54) METHOD FOR TREATMENT OF CONSTIPATION-PREDOMINANT IRRITABLE BOWEL SYNDROME

(75) Inventors: Barry D. Quart, Encinitas, CA (US); David P. Rosenbaum, Waban, MA (US)

(73) Assignee: Napo Pharmaceuticals, Inc., South San Francisco, CA (US)

( * ) Notice: Subject to any disclaimer, the term of this patent is extended or adjusted under 35 U.S.C. 154(b) by 5 days.

(21) Appl. No.: 11/741,796

(22) Filed: Apr. 30, 2007

(65) Prior Publication Data

US 2008/0031983 A1 Feb. 7, 2008

Related U.S. Application Data

(60) Provisional application No. 60/797,076, filed on May 1, 2006.

(51) Int. Cl.
*A01N 65/00* (2006.01)
*A61K 31/74* (2006.01)

(52) U.S. Cl. ..................... 424/725; 424/78.01
(58) Field of Classification Search ........................ None
See application file for complete search history.

(56) References Cited

U.S. PATENT DOCUMENTS

| | | | |
|---|---|---|---|
| 4,698,360 A | 10/1987 | Masquelier | |
| 4,857,327 A | 8/1989 | Virdalm | |
| 5,043,160 A | 8/1991 | Wursch | |
| 5,211,944 A | 5/1993 | Tempesta | |
| 5,234,922 A | 8/1993 | Welsh et al. | |
| 5,494,661 A | 2/1996 | Tempesta | |
| 6,281,240 B1 | 8/2001 | Schultz | |
| 7,208,183 B2 | 4/2007 | Bobrowski | |
| 7,235,573 B2 | 6/2007 | Verkman et al. | |
| 2004/0063695 A1 | 4/2004 | Verkman et al. | |
| 2004/0235800 A1 | 11/2004 | Verkman et al. | |
| 2005/0019389 A1* | 1/2005 | Rozhon et al. | 424/452 |
| 2005/0100535 A1* | 5/2005 | Farmer et al. | 424/93.46 |
| 2007/0104728 A1* | 5/2007 | Olalde Rangel | 424/195.15 |

FOREIGN PATENT DOCUMENTS

| EP | 0481396 | 1/1995 |
|---|---|---|
| WO | WO-0047062 | 8/2000 |

OTHER PUBLICATIONS

Fischer et al., A novel extract SB-300 from the stem bark latex of *Croton lechleri* inhibits CFTR-mediated chloride secretion in human colonic epithelial cells, Journal of Ethnopharmacology, (2004) vol. 93, No. 2/3, pp. 351-357.*
Fischer et al., A novel extract SB-300 from the stem bark latex of *Croton lechleri* inhibits CFTR-mediated chloride secretion in human colonic epithelial cells. Journal of Ethnopharmacology, (2004) vol. 93, No. 2/3, pp. 351-357.
U.S. National Library of Medicine and National Institutes of Health website, <<www.nlm.nih.gov/medlineplus/druginfo/medmaster/ a682280.html>>, entry for loperamide, last revised-Jan. 1, 2002, downloaded from internet on Aug. 27, 2007.
Wood, AJJ, "Irritable Bowel Syndrome," New England Journal of Medicine, Nov. 27, 2003, vol. 349, issue 22, pp. 2136-2146.
Jailwala et al., "Pharmacologic Treatment of the Irritable Bowel Syndrome: A Systematic Review of Randomized, Controlled Trials," Ann Intern Med, 2000, vol. 133, pp. 136-147.
Cremonini et al., "Diagnostic and Therapeutic Strategies in the Irritable Bowel Syndrome," Minerva Med, 2004, vol. 95, No. 5, pp. 427-441.
DiCesare et al., "A double blind, randomized, placebo-controlled study of SP-303 (Provir) in the symptomatic treatment of acute diarrhea among travelers to Jamaica and Mexico," Am. J. Gastroenterol., vol. 97, issue 10, pp. 2585-2588, Oct. 2002.
Miller et al., "Inhibition of Neurogenic Inflammation by the Amazonian Herbal Medicine Sangre de Grado," Journal of Investigative Dermatology, vol. 117, No. 3, pp. 725-730, Sep. 2001.
Hovdenak, N., Scandavanian Journal of Gastroenterology, vol. 22, supp. 130, pp. 81-84, 1987.
Efskind, P., et al., Scandanavian Journal of Gastroenterology, vol. 31, No. 5, pp. 463-468, May 1996.
Miller, M. et al., Am. J. Physiol Gastrointest Liver Physiol., vol. 279, pp. G192-G200, 2000.
Lavo, B., et al., Scandanavian Journal of Gastroenterology, vol. 22, supp. 130, pp. 77-80, 1987.
Cann, P., et al., Digestive Diseases and Sciences, vol. 29, No. 3, pp. 239-247, Mar. 1984.
Black, "The Prophylaxis and Therapy of Secretory Diarrhea," Medical Clinics of North America 66(3): 611-621.
Castelli and Carosi, 1995, "Epidemiology of Traveler's Diarrhea," Chemotherapy 41(suppl. 1): 20-32.
Chen et al., "Studies on the Anti-Tumor, Anti-Bacterial, and Wound-Healing Properties of Dragon's Blood," Planta Med. 1994, 60:541-545.
Driesen et al., 1993, "Studies on Preweaning Piglet Diarrhoea," Australian Veterinary Journal, 70(7): 259-262.

(Continued)

*Primary Examiner*—Michele Flood
*Assistant Examiner*—Qiuwen Mi
(74) *Attorney, Agent, or Firm*—Margaret B. Brivanlou; Michael A. Willis; King & Spalding LLP

(57) ABSTRACT

Methods for treating constipation-predominant irritable bowel syndrome comprise administering to a patient in need thereof a polymeric proanthocyanidin composition from a *Croton* species or *Calophyllum* species in an amount sufficient to treat constipation-predominant irritable bowel syndrome (c-IBS). Treatment of c-IBS includes the treatment of the constipation component of c-IBS as well as the pain and abdominal discomfort associated with c-IBS. In one embodiment, the polymeric proanthocyanidin compound is crofelemer. In addition, methods for treating alternating constipation-predominant/diarrhea-predominant irritable bowel syndrome are an alternative embodiment of the invention.

7 Claims, 6 Drawing Sheets

OTHER PUBLICATIONS

DuPont, 1995, "Pathogenesis of Traveler's Diarrhea," 41 (suppl 1): 33-39.

DuPont, 1995, "Traveler's Diarrhea," Infections of the Gastrointestinal Tract, (Edited by M. Blaser et al., Raven Press, Ltd., New York): 299-310.

Gabriel et al., 1994, "Cystic Fibrosis Heterozygote Resistance to Cholera Toxin in the Cystic Fibrosis Mouse Model," Science 266: 107-109.

Gabriel et al., 1993, "CFTR and Outward Rectifying Chloride Channels are distinct Proteins with a Regulatory Relationship," Nature 363:263-266.

Galvez et al., 1991, "Antidiarrhoeic Activity of *Sclerocarya birrea* Bark Extract and its Active Tannin Constituent in Rats," Phyt. Res. 5:276-278.

Galvez et al., 1993, "Pharmacological Activity of a Procyanidin Isolated from *Sclerocarya birrea* Bark: Antidiarrhoel Activity and Effects on Isolated Guinea-pig ileum," Phyt. Res. 7:25-28.

Gracey, 1986, "Bacterial Diarrhoea," Clinics in Gasteronerology 15(1): 21-37.

Gutzmiller et al., 1996, "Effects of Oral Lactose and Xylose Loads on Blood Glucose, Galactose, Xylose, and Insulin Values in Healthy Calves and Calves with Diarrhea," AJVR 57(4): 560-563.

Harris, 1988, "Review of Selected Bacterial Enterotoxins and their Role in Gastroenteritis," 18: 102-108.

Holland, 1990, "Some Infectious Causes of Diarrhea in Young Farm Animals," Clinical Microbiology Reviews 3(4): 345-375.

Hör et al., 1995, "Inhibition of Intestinal Chloride Secretion by Proanthocyanidins from *Guazuma ulfmifolia*," Planta Med. 61: 208-212.

Hör et al., 1996, "Proanthocyanidin Polymers with Antisecretory Activity and Proanthocyanidin Oligomers from *Guazuma ulmifolia* Bark," Phytochemistry 42(1): 109-119.

König et al., 1994, "Ellagitannins and Complex Tannins from *Quercus petraea* Bark," J. Nat. Prod. 57:1411-1415.

Mouricout, 1991, "Swine and Cattle Enterotoxigenic *Escherichia coli*-mediated Diarrhea. Development of Therapies Based on Inhibition of Bacteria-Host Interactions," Eur. J. Epidemiol. 7(6): 588-604.

Newman et al., 1987, "High-Resolution C NMR Studies of Proanthocyanidin Polymers (Condensed Tannins)," Nag. Res. Comm. 25: 118-124.

Onwukaeme and Lot, 1991, "A Pharmacological Evaluation of *Baphia nitida* Lodd (Leguminosae) Ethanolic Extracts on Rats and Mice," Phytotherapy Res. 5:254-257.

Onwukaeme and Anuforo, 1993, "Phtochemical and Pharmacological Studies on *Pycanthus angolensis* (Welw) Warb (Myristicaceae)," Discovery and Innovation 5:317-322.

Oooms and Degryse, 1986, "Pathogenesis and Pharmacology of Diarrhea," Veterinary Research Communications 10:355-397.

Pallenbach et al., 1993, "Proanthocyanidins from *Quercus petraea* Bark," Planta Med, 59: 264-268.

Persinos et al., 1979, "Errors in Chlorothiazide Bioavailability Estimates Based on a Bratton-Marshall Colorimetric Method for Chlorothiazide in Urine," J. Pharm. Sci. 68: 124.

Sethi, 1977, "Inhibition of RNA-Directed DNA Polymerase Activity of RNA Tumor Viruses by Taspine," Canadian J. Pharm. Sci. 12: 7-9.

Silverstein, 1989, "Procyandin from Black Bean (Phaseolus Vulgars): Effects on Transport of Sodium, Chloride, Glucose, and Alanine in the rat ileum," Washington State University (Dissertation).

Strombeck, 1995, "Diagnosis and Treatment Chronic Diarrhea," The Veterinary Quarterly 17(Suppl. I): S12-S15.

Tanaka et al., 1992, "Tannins and Related Compounds. CXVI. Six New Complex Tannins, Guajavins, Psidinins and Psiguavin from the Bark of *Psidium guajava* L.," Chem. Pharm. Bull. 40: 2092-2098.

Toda et al., 1991, "The Protective Activity of Tea Against Infection by *Vibrio cholerae* 01," J. App. Bact. 70: 109-112.

Ubillas et al., 1994, "SP-303, an Antiviral Oligomeric Proanthocyandin from the Latex of *Croton lecheri* (Sangre de Drago)," Phytomedicine 1: 77-106.

Vermut, 1994, "Rearing and Management of Diarrhoea in Claves to Weaning," Australian Veterinary Journal 71(2): 33-41.

Yoshida et al., 1992, "Tannins and Related Polyphenols of Rosaceous Medicinal Plants. XII. Roshenins A-E, Dimeric Hydrolyzable Tannins from *Rosa henryi* Boul.," Chem. Pharm. Bull. 40: 1997-2001.

Yoshida et al., 1993, "Two Polyphenol Glycosides and Tannins from Rosa-Cymosa," Phytochemistry 32: 1033.

Craig, 1996, "Shaman Gets Positive Efficacy Data on Diarrhea Drug," Bioworld Today 7(164): 1-2.

Foo et al., 1989, "Procyanidin polymers of Douglas Fir bark: structure from degradation with phloroglucinol," Phytochemistry 28:3185-3190.

Foo et al., 1986, "Some Recent Advances in the Chemistry of Condensed Tannins (proanthocyanidin polymers) Relevant to Their Use as Industrial Chemicals," Appita 39:477-480.

Hemingway, 1988, "Reactions At The Interflavanoid Bond Of Proanthocyanidins" in *Proceedings of the North American Tannin Conference. Chemistry and Significance of Condensed Tannins*, Hemingway and Karchesy (eds.), Plenum Press, NY, pp. 265-283.

Porter, 1989. Methods in Plant Biochemistry 1:389-418.

Porter et al., 1986, "The Conversion Of Procyanidins and Prodelphinidins to Cyanidin and Delphinidin," Phytochemistry 25:223-230.

Remington's Pharmaceutical Sciences, 16$^{th}$ Edition, 1980, Mack Publishing Inc., Easton, pp. 87:1530 and 1585-1593.

Thompson et al., 1972, Plant Proanthocyanidins, Part I. Introduction: the Isolation, Structure and Distribution in Nature of Plant Procyanidins J.C.S. Perkin 1:1387-1399.

Davenport et al., "A Novel Plant Derived Inhibitor of cAMP-Mediated Cl Secretion" Pulmonology S13 abstract 34 (Aug. 16, 1996).

The Biologically Active Constituents of "Snagre De Drago" A Traditional South American Drug, 1992.

Schuier M., et al., Cocoa-Related Flavonoids Inhibit CFTR-Mediated Chloride Transport across T84 Human Colon Epithelia,: J. Nutr., vol. 135, pp. 2320-2325, Oct. 2005.

Martin, et al., "Cyclooxygenase-2 Inhibition Sensitizes Human Colon Carcinoma Cells to TRAIL-Induced Apoptosis through Clustering of DR5 and Concentrating Death-Inducing Signaling Complex Components Into Ceramide Enriched Caveolae," Cancer Res 2006; 65:(24) Dec. 15, 2005, pp. 11447-11458.

Mangel et al., "Evaluation of Crofelemer in the Treatment of Diarrhea- Predominant Irritable Bowel Syndrome (dIBS) Patients," unpublished manuscript.

Pieters, L., "The Biologically Active Constituents of "Sangre De Drago" A Traditional South American Drug." University of Antwerp, doctoral dissertation in the Department Farmaceutische Wetenschappen, 1992.

* cited by examiner ly of this application shall not be construed as an admission that such reference is available as prior art for the present application.

METHOD FOR TREATMENT OF CONSTIPATION-PREDOMINANT IRRITABLE BOWEL SYNDROME

This application claims benefit of priority to U.S. provisional patent application 60/797,076, filed May 1, 2006, the contents of which are hereby incorporated by reference.

BACKGROUND OF THE INVENTION

Irritable bowel syndrome (IBS) is a common functional disorder of the bowel that has a pronounced effect on quality of life. A defining characteristic of IBS is abdominal discomfort or pain. The Rome II Diagnostic Criteria (a system for diagnosing functional gastrointestinal disorders based on symptoms) for IBS is as follows: at least 12 weeks or more, which need not be consecutive, in the preceding 12 months of abdominal discomfort or pain that is accompanied by at least two of the following features: (1) it is relieved with defecation, and/or (2) onset is associated with a change in frequency of stool, and/or (3) onset is associated with a change in form (appearance) of stool.

Other symptoms that support the diagnosis of IBS include pain; abnormal stool passage (straining, urgency, or feeling of incomplete evacuation); passage of mucus; and bloating or feeling of abdominal distension. Patients can be sub-divided by their underlying bowel habits: (i) diarrhea-predominate IBS, (ii) constipation-predominate IBS, and (ii) constipation alternating with diarrhea (alternating IBS).

The pathophysiology of IBS is poorly understood despite the fact that about a quarter of the population in the UK may exhibit the symptoms, and approximately 15 percent of U.S. adults report symptoms that are consistent with the diagnosis of IBS. It is estimated that only 25 percent of persons with IBS seek medical care. In addition, patients diagnosed with IBS are at increased risk for other, non-gastrointestinal functional disorders such as fibromyalgia and interstitial cystitis.

IBS is the most common diagnosis made by gastroenterologists in the U.S., and accounts for 12 percent of visits to primary care providers. Approximately $8 billion in direct medical costs and $25 billion in indirect costs are spent annually in the U.S. for diagnosing and treating IBS. Thus, IBS accounts for a large proportion of annual healthcare costs in the U.S.

Primary treatment of IBS involves counseling and dietary modification. Drug therapy is considered to be beneficial if directed at individual symptoms. For diarrhea predominant cases, antidiarrheal drugs such as loperamide can be used, which treat diarrhea, but not abdominal pain. Since abdominal pain is one of the defining characteristic of IBS, antidiarrheal drugs do not adequately treat IBS (Jailwala et al., 2000, *Ann Intern Med.* 2000; 133:136-147; Cremonini et al., 2004, *Minerva Med* 95:427-441). For constipation predominant cases, ispaghula is often used to increase dietary fiber. Where patients have pain and distension as predominant symptoms, anti-spasmolytics are commonly used. Mebeverine and peppermint oil are often used in such cases. Other agents that have been tried for treating IBS include beta-blockers, naloxone, ondansetron, calcium channel blockers, simethicone, leuprorelin, octreotide and cholecystokinin antagonists with variable results (Martindale, *The Extra Pharmacopoeia,* 31st Edition (1996) p. 1197).

U.S. Pat. Nos. 5,211,944 and 5,494,661 to Tempesta disclose the use of a proanthocyanidin polymeric composition isolated from *Croton* spp. or *Calophyllum* spp. for the treatment of viral infections. Rozhon et al., U.S. Patent Publication No. 2005/0019389, disclose the use of a proanthocyanidin polymeric composition isolated from *Croton* spp. or *Calophyllum* spp. for the treatment of secretory or traveler's diarrhea. Di Cesare et al., 2002, Am J Gastroenterol 10:2585-2588 disclose a clinical trial of crofelemer as a treatment for traveler's diarrhea compared to placebo. Dosages used in this study were 500 mg/day (125 four times a day); 1000 mg/day (250 mg four times a day); and 2000 mg/day (500 mg four times a day) for two days. The study showed that the composition was useful for the amelioration of stool frequency and gastrointestinal symptoms in patients with traveler's diarrhea.

Citation or identification of any reference in this section or any other section of this application shall not be construed as an admission that such reference is available as prior art for the present application.

SUMMARY OF THE INVENTION

The present invention relates to methods for treating at least one symptom of constipation-predominant irritable bowel syndrome (c-IBS) by administering a composition or extract obtained from a *Croton* species or *Calophyllum* species. In one embodiment, the composition is a latex from a *Croton* species or *Calophyllum* species. In yet another embodiment, the composition is a polymeric proanthocyanidin composition from a *Croton* species or *Calophyllum* species. Exemplary symptoms of c-IBS include pain; abdominal discomfort, such as abdominal fullness, bloating or swelling; abnormal stool frequency, i.e., fewer than three bowel movements per week; hard or lumpy stools; straining during a bowel movement; urgency and feeling of incomplete bowel movement. Thus, in one embodiment, the invention provides a method for the treatment of one or more symptoms of c-IBS comprising administering to a patient in need of such treatment, an amount of a polymeric proanthocyanidin composition from a *Croton* species or *Calophyllum* species effective to treat the one or more symptoms of c-IBS. In preferred embodiments, the dosage of the composition is bioequivalent to orally administered enteric coated crofelemer at a dosage of about 250 mg per day to about 4000 mg per day. In one embodiment, bioequivalency is a sufficient dose of a composition of the invention to produce the desired effects as seen with another composition at a particular dosage, e.g., enteric coated crofelemer at a dosage of about 250 mg per day to about 4000 mg per day. In another embodiment, bioequivalency is as defined by, or is as determined in accordance with methods approved by, the U.S. Food and Drug Administration. In a particular embodiment, the composition of the invention is co-administered with an anti-inflammatory or analgesic compound, which compound is preferably not systemically absorbed or is modified such that the compound is not systemically absorbed. Such compounds include 5-ASA, sulfasalazine, mesalamine, APAZA, celecoxib and rofecoxib.

In a particular embodiment, the present invention is directed to a method of treating pain associated with c-IBS comprising administering to a patient in need of such treatment, an amount of a polymeric proanthocyanidin composition from a *Croton* species or *Calophyllum* species effective to treat pain associated with c-IBS. In another embodiment, the present invention is directed to a method of treating abdominal discomfort associated with c-IBS comprising administering to a patient in need of such treatment, an amount of a polymeric proanthocyanidin composition from a *Croton* species or *Calophyllum* species effective to treat abdominal discomfort associated with c-IBS. Optionally, analgesic or anti-inflammatory agents can be co-administered with the composition. In particular, the composition is formulated or is modified such that it is not systemically absorbed, i.e., only 20%, 15%, 10%, 5%, 4%, 3%, 2%, 1%, 0.5% or less than 0.5% absorbed of the dosage given.

In yet another embodiment, the present invention is directed to a method of treating abnormal stool frequency associated with c-IBS comprising administering to a patient in need of such treatment, an amount of a polymeric proanthocyanidin composition from a *Croton* species or *Calophyllum* species effective to treat the abnormal stool frequency associated with c-IBS, e.g., by increasing the number of stools per week.

Exemplary polymeric proanthocyanidin compositions useful in the present invention are preferably isolated from a *Croton* species or *Calophyllum* species. For example, the composition can be a proanthocyanidin polymer composition isolated from a *Croton* spp. or *Calophyllum* spp by any method known in the art. For example, the proanthocyanidin polymer composition may be isolated from a *Croton* spp. or *Calophyllum* spp. by the method disclosed in Example 2, infra, or disclosed in U.S. Pat. No. 5,211,944 or in Ubillas et al., 1994, *Phytomedicine* 1: 77-106. PCT application PCT/US00/02687, published as WO 00/47062, discloses a method of manufacturing a proanthocyanidin polymeric composition isolated from *Croton* spp. or *Calophyllum* spp. In preferred embodiment, the composition is enteric protected, e.g., enteric coated. Thus, in a particular embodiment, the present invention is directed to a method of treating abnormal stool frequency associated with c-IBS comprising administering to a patient in need of such treatment, an amount of a polymeric proanthocyanidin composition isolated from *Croton* spp. or *Calophyllum* spp. effective to treat the abnormal stool frequency associated with c-IBS, in which said amount is bioequivalent to an orally administered dose of about 250 mg per day to about 4000 mg per day of enteric protected crofelemer.

In one preferred embodiment, a proanthocyanidin polymer composition of the invention is crofelemer. Crofelemer (CAS 148465-45-6) is an oligomeric proanthocyanidin of varying chain lengths derived from the Dragon's Blood of *Croton lecheri* of the family Euphorbiaceae. Crofelemer has an average molecular weight of approximately 1900 daltons to approximately 2700 daltons. The monomers comprising crofelemer comprise catechin, epicatechin, gallocatechin, and epigallocatechin. The chain length of crofelemer ranges from about 3 to about 30 units with an average chain length of about 8 units. Thus, in a preferred embodiment, the present invention is directed to a method of treating abnormal stool frequency associated with c-IBS comprising orally administering to a patient in need of such treatment, an amount of enterically-protected crofelemer effective to treat the abnormal stool frequency associated with c-IBS, in which said amount is between about 250 mg per day and about 4000 mg per day. In certain embodiments where crofelemer is otherwise formulated (not enterically protected), the dosage of crofelemer administered is bioequivalent to a dosage of about 250 mg per day to about 4000 mg per day of orally administered enterically-protected crofelemer. For example, such formulation is a delayed release formulation.

In an alternative embodiment, the present invention is directed to a method for treating one or more symptoms of alternating constipation-predominant/diarrhea-predominant irritable bowel syndrome (a-IBS) comprising administering to a patient in need of such treatment, an amount of an extract or latex from a *Croton* species or *Calophyllum* species effective to treat the one or more symptoms of a-IBS. In one embodiment, the composition is a polymeric proanthocyanidin composition from a *Croton* species or *Calophyllum* species. In one aspect of this embodiment, the present invention is directed to a method for treating pain associated with alternating constipation-predominant/diarrhea-predominant irritable bowel syndrome (a-IBS) comprising administering to a patient in need of such treatment, an amount of a polymeric proanthocyanidin composition from a *Croton* species or *Calophyllum* species effective to treat the pain associated with a-IBS. In preferred embodiments, the dosage of the composition is bioequivalent to orally administered enteric coated crofelemer at a dosage of about 50 mg per day to about 4000 mg per day. In one embodiment, bioequivalency is a sufficient dose of a composition of the invention to produce a similar therapeutic effect as seen with another composition at a particular dosage, e.g., enteric coated crofelemer at a dosage of about 250 mg per day to about 4000 mg per day. In another embodiment, bioequivalency is as defined by, or is as determined in accordance with methods approved by, the U.S. Food and Drug Administration. Individuals suffering from a-IBS experience symptoms associated with both c-IBS and d-IBS depending on the type of IBS the patient is experiencing at a particular time. Thus, an a-IBS symptom that can be treated by administering a composition of the invention includes, pain, abdominal discomfort, abnormal stool frequency, abnormal stool consistency, presence of urgency, diarrhea, and constipation.

DETAILED DESCRIPTION OF THE INVENTION

Figure 1:
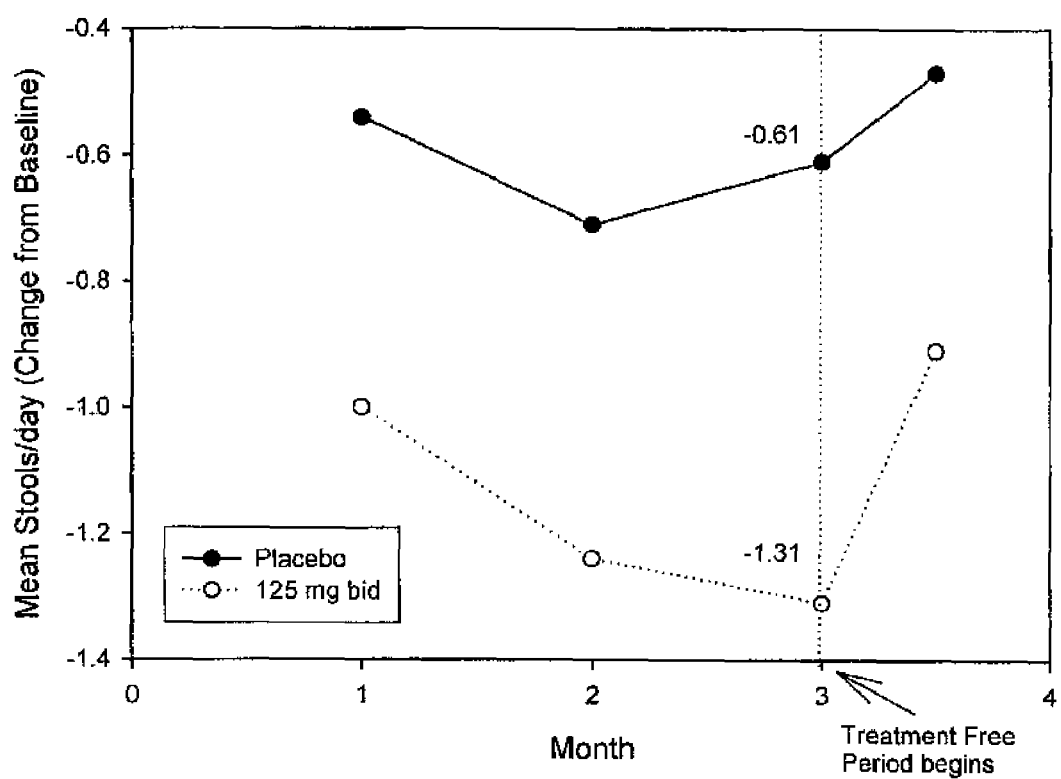
FIG. 1 is a graph illustrating the Effect of Crofelemer 125 mg bid on Stool Frequency in Females.
Figure 2:
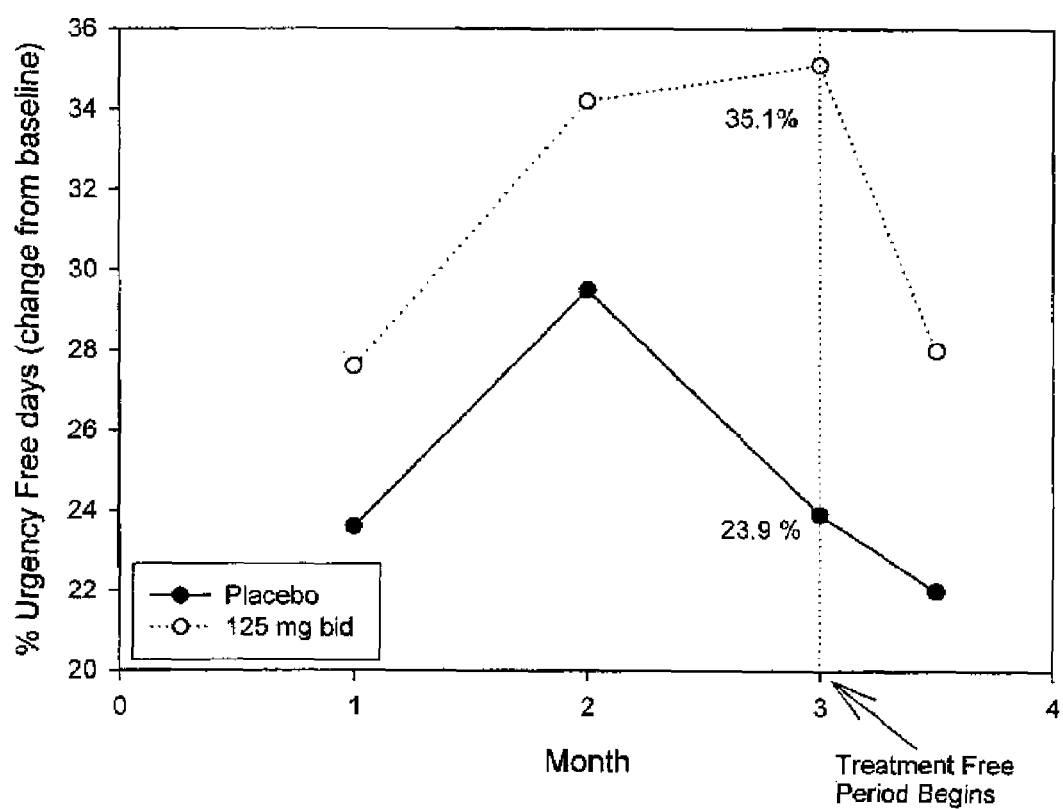
FIG. 2 is a graph illustrating the Effect of Crofelemer 125 mg bid on Urgency in Females.
Figure 3:
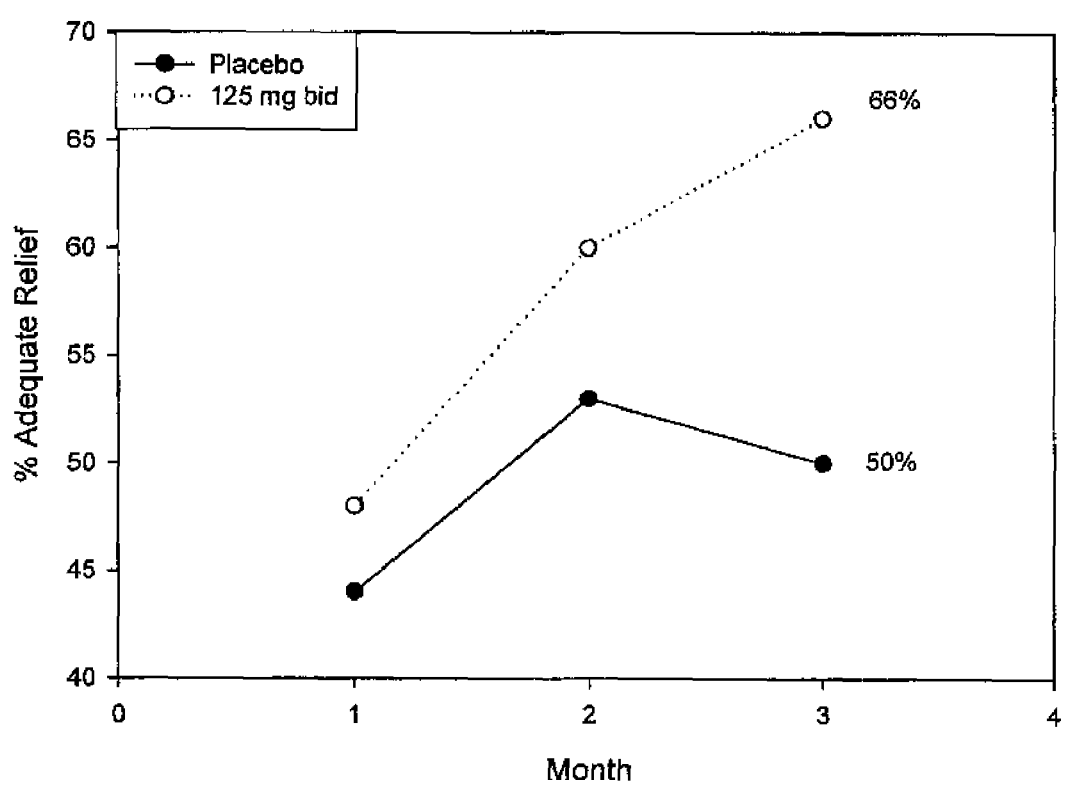
FIG. 3 is a graph illustrating the Effects of Crofelemer on Adequate Relief of IBS Symptoms in Females.

The present invention relates to methods for treating at least one symptom of constipation-predominant irritable bowel syndrome (c-IBS) by administering a composition, e.g., an extract or latex, from a *Croton* species or *Calophyllum* species, such as a polymeric proanthocyanidin composition. Exemplary symptoms of c-IBS include pain; abdominal discomfort, such as abdominal fullness, bloating or swelling; abnormal stool frequency, i.e., fewer than three bowel movements per week; hard or lumpy stools; straining during a bowel movement; urgency and feeling of incomplete bowel movement. Thus, in one embodiment, the invention provides a method for the treatment of one or more symptoms of c-IBS comprising administering to a patient in need of such treatment, an amount of a polymeric proanthocyanidin composition from a *Croton* species or *Calophyllum* species effective to treat the one or more symptoms of c-IBS.

The present invention is based, in part, on the discovery that an extract or latex from *Croton* spp. or *Calophyllum* spp., including polymeric proanthocyanidin compositions isolated from *Croton* spp. or *Calophyllum* spp., including crofelemer, alleviate pain, abdominal discomfort and constipation associated with IBS. Additionally, the present invention is based, in part, on the discovery that an extract or latex from *Croton* spp. or *Calophyllum* spp., including polymeric proanthocyanidin compositions isolated from *Croton* spp. or *Calophyllum* spp., including crofelemer, alleviate symptoms of c-IBS, such as abnormal stool frequency at dosages higher than those useful to treat symptoms of diarrhea-predominant IBS.

In one preferred embodiment, the composition of the invention is a proanthocyanidin polymer composition. In another preferred embodiment, the composition is an aqueous soluble proanthocyanidin polymer composition. In another preferred embodiment, the compositions of the present invention are not substantially systemically absorbed or are modified not to be systemically absorbed when administered orally.

Proanthocyanidins are a group of condensed tannins. Tannins are found in a wide variety of plants and are classified as either hydrolyzable or condensed. Many plants used in traditional medicine as treatment or prophylaxis for diarrhea have been found to contain tannins and proanthocyanidins in particular (see, e.g., Yoshida et al., 1993, *Phytochemistry* 32:1033; Yoshida et al., 1992, *Chem. Pharm. Bull.*, 40:1997; Tamaka et al., 1992, *Chem. Pharm. Bull.* 40:2092).

Proanthocyanidins are comprised of at least two or more monomer units that may be of the same or different monomeric structure. The monomer units (generally termed "leucoanthocyanidin") are generally monomeric flavonoids which include catechins, epicatechins, gallocatechins, galloepicatechins, flavanols, flavonols, and flavan-3,4-diols, leucocyanidins and anthocyanidins. Therefore, the polymer chains are based on different structural units, which create a wide variation of polymeric proanthocyanidins and a large number of possible isomers (Hemingway et al., 1982, J. C. S. *Perkin*, 1:1217). Larger polymers of the flavonoid 3-ol units are predominant in most plants, and are found with average molecular weights above 2,000 daltons, containing 6 or more units (Newman et al., 1987, *Mag. Res. Chem.*, 25:118).

Proanthocyanidin polymers are found in a wide variety of plants, particularly those with a woody habit of growth (e.g., *Croton* spp. and *Calophyllum* spp.). A number of different *Croton* tree species, including *Croton sakutaris, Croton gossypifolius, Croton palanostima, Croton lechleri, Croton erythrochilus* and *Croton draconoides*, found in South America, produce a red viscous latex sap called Sangre de Drago or "Dragon's Blood". This red, viscous latex is widely known for its medicinal properties. For example, U.S. Pat. No. 5,211,944 first described the isolation of an aqueous soluble proanthocyanidin polymer composition from *Croton* spp. and the use of the composition as an antiviral agent (See also Ubillas et al., 1994, *Phytomedicine*, 1:77). The proanthocyanidin polymer composition was shown to have antiviral activity against a variety of viruses including, respiratory syncytial, influenza, parainfluenza and herpes viruses. U.S. Pat. No. 5,211,944 also discloses the isolation of an aqueous soluble proanthocyanidin polymer composition from *Calophyllum inophylum* and the use of this composition as an antiviral agent.

Exemplary proanthocyanidin polymer compositions useful in the present invention are preferably isolated from a *Croton* spp. or *Calophyllum* spp by any method known in the art. For example, the proanthocyanidin polymer composition may be isolated from a *Croton* spp. or *Calophylum* spp. by the method disclosed in Example 2, infra, or disclosed in U.S. Pat. No. 5,211,944 or in Ubillas et al., 1994, *Phytomedicine* 1: 77-106.

In one preferred embodiment, a proanthocyanidin polymer composition of the invention is crofelemer. Crofelemer (CAS 148465-45-6) is an oligomeric proanthocyanidin of varying chain lengths derived from the Dragon's Blood of *Croton lecheri* of the family Euphorbiaceae. Crofelemer has an average molecular weight of approximately 1900 daltons to approximately 2700 daltons. The monomers comprising crofelemer comprise catechin, epicatechin, gallocatechin, and epigallocatechin. The chain length of crofelemer ranges from about 3 to about 30 units with an average chain length of about 8 units. The structure of crofelemer is shown below.

Another illustrative method for isolating crofelemer can be found in U.S. Patent Publication No. 2005/0019389, the contents of which are expressly incorporated herein. PCT application PCT/US00/02687, published as WO 00/47062, discloses a method of manufacturing a proanthocyanidin polymeric composition isolated from *Croton* spp. or *Calophyllum* spp.

In other embodiments of the invention, the composition useful in the methods of the invention is a raw latex obtained from a *Croton* species or a *Calophyllum* species or an extract obtained from a *Croton* species or a *Calophyllum* species that are not specifically polymeric proanthocyanidin compositions. Exemplary extracts are described in Persinos et al., 1979, J. Pharma. Sci. 68:124 and Sethi, 1977, Canadian J. Pharm. Sci. 12:7.

In a preferred embodiment, the compositions used in the methods of the invention are not substantially systemically absorbed when administered orally, i.e., only 20%, 15%, 10%, 5%, 4%, 3%, 2%, 1%, 0.5% or less than 0.5% absorbed of the dosage given. Drugs that are systemically absorbed when delivered orally can be modified to prevent systemic absorption, if necessary. Such modifications are known in the art. For example, a composition of the invention may be covalently attached to a non-systemically absorbed compound that is substantially inert in the gastrointestinal tract and does not interfere with the function of the composition. Such non-systemically absorbed compounds include various polymers. The polymers that are preferably used with the compositions of the invention resist degradation and absorption in the gastrointestinal system, i.e., the polymers do not substantially break down under physiological conditions in the stomach and intestines into fragments which are absorbable by body tissues. Polymers that have a non-hydrolyzable backbone which is substantially inert under conditions encountered in the gastrointestinal tract, are preferred. Such polymers will preferably have a sufficiently high molecular weight to resist absorption, partially or completely, from the gastrointestinal tract into other parts of the body. The polymers can have molecular weights ranging from about 500 Daltons to about 500,000 Daltons, preferably from about 2,000 Daltons to about 150,000 Daltons. Examples of suitable polymers include but are not limited to, polysaccharides, polyethylene glycol polymers, cellulosic polymers, polystyrene polymers, polyacrylate polymers, and polyamide polymers.

The present invention encompasses methods for treating and/or preventing one or more symptoms associated with constipation-predominant irritable bowel syndrome (c-IBS), in warm blooded animals, including male and female humans, which symptoms include, but are not limited to, pain, abdominal discomfort and abnormal stool frequency. The methods of the invention generally comprise administering to a subject in need of c-IBS treatment a polymeric proanthocyanidin composition in accordance with the invention. In a preferred embodiment, the composition is orally administered and is not systemically absorbed. In another embodiment, the composition is enteric protected. Preferably, the patient is a human female.

In one embodiment, the present invention provides a method of treating pain associated with c-IBS comprising administering to a patient in need of such treatment, an amount of a polymeric proanthocyanidin composition effective to treat pain associated with c-IBS, in which said amount is bioequivalent to an orally administered dose of about 250 mg per day to about 4000 mg per day of crofelemer. In another embodiment, the present invention provides a method of treating abdominal discomfort associated with c-IBS comprising administering to a patient in need of such treatment, an amount of a polymeric proanthocyanidin composition effective to treat abdominal discomfort associated with c-IBS, in which said amount is bioequivalent to an orally administered dose of about 250 mg per day to about 4000 mg per day of crofelemer. In certain embodiments, the composition is co-administered with an analgesic and/or anti-inflammatory compound.

Pain and discomfort can be measured by any method known in the art, for instance on a pain or discomfort scale in which a patient assigns the level of pain or discomfort on a scale of 0 to 5, with 0 being no pain or discomfort and 5 being assigned the highest level of pain or discomfort. In certain embodiments, the alleviation of pain or discomfort is measured by a lowering of the average level of pain or discomfort, an increase in the number of pain or discomfort-free days. In certain embodiments, the number of pain or discomfort-free days is increased by at least 5%, 10%, 15%, 20%, 25%, 30%, 35%, 40%, 45%, or by at least 50% compared to before treatment. In other embodiments, the level of pain or discomfort decreased by at least 0.1, 0.2, 0.3, 0.4 or by at least 0.5 units compared to before treatment, or even by at least 1 unit, 1.5 units, or 2 units.

In another embodiment, the present invention provides a method of treating abnormal stool frequency associated with c-IBS comprising administering to a patient in need of such treatment, an amount of a polymeric proanthocyanidin composition effective to treat the abnormal stool frequency associated with c-IBS.

In particular embodiments, stool frequency is increased by at least 10%, 20%, 30%, 40% or 50% or more compared to before treatment. In other embodiments, stool frequency is increased by at least one bowel movement per day compared to before treatment. In yet another embodiment, stool frequency is increased by at least one, two, three or four additional bowel movements per week compared to before treatment. In certain embodiments, stool consistency is also decreased, i.e., there is an increase in the amount of water in the stool, by at least 10%, 20%, 25%, 30%, 40%, or 50% compared to before treatment.

In an alternative embodiment, the present invention encompasses methods for treating and/or preventing one or more symptoms associated with alternating diarrhea/constipation-predominant irritable bowel syndrome (a-IBS), in warm blooded animals, including male and female humans, which symptoms include, but are not limited to, pain, abdominal discomfort, abnormal stool frequency, abnormal stool consistency, diarrhea, and constipation. The methods of the invention generally comprise administering to a subject in need of a-IBS treatment a polymeric proanthocyanidin composition in accordance with the invention. In a preferred embodiment, the composition is orally administered and is not systemically absorbed. In another embodiment, the composition is enteric protected. Preferably, the patient is a human female.

In one embodiment, the present invention provides a method of treating pain associated with a-IBS comprising administering to a patient in need of such treatment, an amount of a polymeric proanthocyanidin composition effective to treat pain associated with a-IBS. In another embodiment, the present invention provides a method of treating abdominal discomfort associated with a-IBS comprising administering to a patient in need of such treatment, an amount of a polymeric proanthocyanidin composition effective to treat abdominal discomfort associated with a-IBS. In certain embodiments, the composition is co-administered with an analgesic and/or anti-inflammatory compound. Pain and discomfort can be measured by any method known in the art, for instance on a pain or discomfort scale in which a patient assigns the level of pain or discomfort on a scale of 0 to 5, with 0 being no pain or discomfort and 5 being assigned the highest level of pain or discomfort. In certain embodiments, the alleviation of pain or discomfort is measured by a lowering of the average level of pain or discomfort, an increase in the number of pain- or discomfort-free days. In certain embodiments, the number of pain- or discomfort-free days is increased by at least 5%, 10%, 15%, 20%, 25%, 30%, 35%, 40%, 45%, or by at least 50% compared to before treatment. In other embodiments, the level of pain or discomfort decreased by at least 0.1, 0.2, 0.3, 0.4 or by at least 0.5 units compared to before treatment.

In another embodiment, the present invention provides a method of treating constipation associated with a-IBS comprising administering to a patient in need of such treatment, an amount of a polymeric proanthocyanidin composition effective to treat the constipation associated with a-IBS.

In particular embodiments, stool frequency is increased by at least 10%, 20%, 30%, 40% or 50% or more compared to before treatment. In other embodiments, stool frequency is increased by at least one bowel movement per day compared to before treatment. In yet another embodiment, stool frequency is increased by at least one, two, three or four additional bowel movements per week compared to before treatment. In certain embodiments, stool consistency is also decreased, i.e., there is an increase in the amount of water in the stool, by at least 10%, 20%, 25%, 30%, 40%, or 50% compared to before treatment.

In another embodiment, the present invention provides a method of treating diarrhea associated with a-IBS comprising administering to a patient in need of such treatment, an amount of a polymeric proanthocyanidin composition isolated from *Croton* spp. or *Calophyllum* spp. effective to treat the diarrhea associated with a-IBS, in which said amount is bioequivalent to an orally administered dose of about 50 mg per day to about 4000 mg per day of crofelemer. In yet another embodiment, the present invention provides a method of treating abnormal stool frequency, abnormal stool consistency or presence of urgency associated with a-IBS comprising administering to a patient in need of such treatment, an amount of a polymeric proanthocyanidin composition isolated from *Croton* spp. or *Calophyllum* spp. effective to treat the abnormal stool frequency, abnormal stool consistency or presence of urgency associated with a-IBS, in which said amount is bioequivalent to an orally administered dose of about 50 mg per day to about 4000 mg per day of crofelemer. In particular embodiments, stool frequency is decreased by at least 10%, 20%, 30%, 40% or 50% compared to before treatment. In other embodiments, stool frequency is decreased by at least one bowel movement per day compared to before treatment. In other embodiments, stool consistency is increased, i.e., there is a decrease in the amount of water in the stool, by at least 10%, 20%, 25%, 30%, 40%, or 50% compared to before treatment. In yet other embodiments, presence of urgency is decreased by at least 10%, 20%, 30%, 40%, or by at least 50% compared to before treatment.

The compositions of the invention can be administered in a single or a divided dosage from one, two, three or four times per day. In a particular embodiment, the composition is administered twice daily. In yet another embodiment, the composition is administered twice daily for at least two consecutive days. In yet another embodiment, the composition is administered for at least a period of time selected from the group consisting of 24 hours, 48 hours, 72 hours, 96 hours, one week, two weeks, one month, two months, and three months. In certain embodiments, where c-IBS or a-IBS is a chronic condition, the composition is taken indefinitely.

The polymeric proanthocyanidin compositions of the present invention are preferably administered orally. In certain embodiments, however, methods of administering a composition of the invention include, but are not limited to, parenteral administration (e.g., intradermal, intramuscular, intraperitoneal, intravenous and subcutaneous), and mucosal (e.g., intranasal route). In other embodiments, a composition is administered intramuscularly, intravenously, or subcutaneously. Compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local.

In certain preferred embodiments of the present invention, the polymeric proanthocyanidin composition is crofelemer (CAS 148465-45-6). In other preferred aspects, crofelemer is administered orally. In yet other preferred embodiments, the composition is formulated so as to protect the composition from the stomach environment, i.e., from the acidic environment and digestive proteins found in the stomach. In a preferred embodiment, administration is by oral route and the composition is enteric protected crofelemer.

In certain preferred embodiments, crofelemer is orally administered in an enteric protected form (enteric coated) in a total amount of not less than about 250 mg/day. As used herein, about means within the margin of error. In specific embodiments, the enteric coated crofelemer is orally administered to a subject suffering from c-IBS in an amount of from about 250 mg/day to 4000 mg/day. In other specific embodiments, where the subject is suffering from a-IBS, the enteric coated crofelemer is orally administered in an amount of from about 50 mg/day to 4000 mg/day. In another embodiment, the enteric coated crofelemer is orally administered to a subject in a total amount of not less than about 500 mg/day. In specific embodiments, the enteric coated crofelemer is orally administered to a subject in an amount of from about 250 mg/day to about 2000 mg/day. In other embodiments, the enteric coated crofelemer is orally administered to a subject at not less than about 1750 mg/day, about 1700 mg/day, about 1650 mg/day, about 1600 mg/day, about 1550 mg/day, about 1500 mg/day, about 1450 mg/day, about 1400 mg/day, about 1350 mg/day, about 1300 mg/day, about 1250 mg/day, 1200 mg/day, about 1150 mg/day, about 1100 mg/day, about 1050 mg/day, about 1000 mg/day, about 950 mg/day, about 900 mg/day, about 850 mg/day, about 800 mg/day, about 750 mg/day, about 700 mg/day, 650 mg/day, about 600 mg/day, about 550 mg/day, about 500 mg/day, about 450 mg/day, about 400 mg/day, about 350 mg/day, about 300 mg/day, or about 250 mg/day of orally administered enteric coated crofelemer. In yet another embodiment, the enteric coated crofelemer is orally administered to a subject in an amount from about 500 mg/day to 1000 mg/day. In other embodiments, the enteric coated crofelemer is orally administered to a subject in an amount of from about 250 mg/day to about 2000 mg/day, from about 250 mg/day to about 1000 mg/day, from about 250 mg/day to about 750 mg/day, from about 250 mg/day to about 500 mg/day, from about 350 mg/day to about 650 mg/day, or from about 500 mg/day to about 750 mg/day. In other particular embodiments, the total dosage of the enteric coated crofelemer orally administered to a subject is not less than about 250 mg, about 255 mg, about 260 mg, about 265 mg, about 285 mg, about 290 mg, about 295 mg, about 315 mg, about 320 mg, about 325 mg, about 345 mg, about 350 mg, about 355 mg, about 375 mg, about 380 mg, about 385 mg, about 405 mg, about 410 mg, about 415 mg, about 435 mg, about 440 mg, about 445 mg, about 465 mg, about 470 mg, about 475 mg, about 495 mg, about 500 mg, about 505 mg, about 525 mg, about 530 mg, about 535 mg, about 555 mg, about 560 mg, about 565 mg, about 585 mg, about 590 mg, about 595 mg, about 615 mg, about 620 mg, about 625 mg, about 645 mg, about 650 mg, about 655 mg, about 675 mg, about 680 mg, about 685 mg, about 705 mg, about 710 mg, about 715 mg, about 270 mg, about 275 mg, about 280 mg, about 300 mg, about 305 mg, about 310 mg, about 330 mg, about 335 mg, about 340 mg, about 360 mg, about 365 mg, about 370 mg, about 390 mg, about 395 mg, about 400 mg, about 420 mg, about 425 mg, about 430 mg, about 450 mg, about 455 mg, about 460 mg, about 480 mg, about 485 mg, about 490 mg, about 510 mg, about 515 mg, about 520 mg, about 540 mg, about 545 mg, about 550 mg, about 570 mg, about 575 mg, about 580 mg, about 600 mg, about 605 mg, about 610 mg, about 630 mg, about 635 mg, about 640 mg, about 660 mg, about 665 mg, about 670 mg, about 690 mg, about 695 mg, about 700 mg, about 720 mg, about 725 mg, about 730 mg, about 735 mg, about 740 mg, about 745 mg, about 750 mg, about 755 mg, about 760 mg, about 765 mg, about 770 mg, about 775 mg, about 780 mg, about 785 mg, about 790 mg, about 795 mg, about 800 mg, about 805 mg, about 810 mg, about 815 mg, about 820 mg, about 825 mg, about 830 mg, about 835 mg, about 840 mg, about 845 mg, about 850 mg, about 855 mg, about 860 mg, about 865 mg, about 870 mg, about 875 mg, about 880 mg, about 885 mg, about 890 mg, about 895 mg, about 900 mg, about 905 mg, about 910 mg, about 915 mg, about 920 mg, about 925 mg, about 930 mg, about 935 mg, about 940 mg, about 945 mg, about 950 mg, about 955 mg, about 960 mg, about 965 mg, about 970 mg, about 975 mg, about 980 mg, about 985 mg, about 990 mg, about 995 mg, or not less than about 1000 mg, once, twice, or three-times per day.

In other embodiments of the invention, the composition, the proanthocyanidin polymer composition is preferably given at a dosage that is bioequivalent to orally administered enteric coated crofelemer at a dosage of about 250 mg per day to about 4000 mg/day or any of the doses listed above.

In a preferred embodiment, crofelemer is enteric coated so as to protect it from degradation by the acidic conditions of the stomach and/or from interactions with proteins, such as pepsin, present in the stomach, i.e., an enteric protected formulation. In a specific embodiment, crofelemer is in tablet form. In yet another specific embodiment, the tablet is enteric coated, e.g., EUDRAGIT®. In a preferred embodiment, crofelemer is formulated as an enteric coated bead or granule in an enteric coated capsule shell. In another embodiment, crofelemer is formulated in a delayed release composition, e.g., Merck GEM, Alza OROS, wax matrix (release is primarily delayed until after the formulation passes out of the stomach and into the intestine).

In certain embodiments, the composition is formulated with a compound or compounds which neutralize stomach acid. Alternatively, the pharmaceutical composition containing the composition is administered either concurrent with or subsequent to or after administration of a pharmaceutical composition which neutralize stomach acid. Compounds, such as antacids, which are useful for neutralizing stomach acid include, but are not limited to, aluminum carbonate, aluminum hydroxide, bismuth subnitrate, bismuth subsalicylate, calcium carbonate, dihydroxyaluminum sodium carbonate, magaldrate, magnesium carbonate, magnesium hydroxide, magnesium oxide, and mixtures thereof. Compounds that are able to reduce the secretion of stomach acid and/or are able to reduce the acidity of stomach fluid are well known in the art and include, but are not limited to, antacids (aluminum hydroxide, aluminum carbonate, aluminum glycinate, magnesium oxide, magnesium hydroxide, magnesium carbonate, calcium carbonate, sodium bicarbonate), stomach acid blockers (cimetidine (Tagamet™), famotidine (Mylanta™, Pepcid™), nizatidine (Axid™), ranitidine (Zantac™), omeprazole (Zegerid™)) and a combination of any of the foregoing. In general, any drug that has been approved for sale by the relevant government agency and is able to reduce the production of stomach acid and/or reduce the acidity of stomach fluid can be administered in combination with an inhibitor molecule, such as crofelemer, in accordance with the methods of the invention.

In other embodiments, the composition is administered with other compounds which are useful in treating constipation or pain, which compounds are preferably not systemically absorbed. Such compounds include 5-ASA, sulfasalazine, mesalamine, APAZA, celecoxib and rofecoxib.

In a particular embodiment where crofelemer is not enteric coated, crofelemer is formulated with one or more compounds that are able to reduce the secretion of stomach acid and/or able to reduce the acidity of stomach fluid. Preferably, the dosage of crofelemer to be given in this formulation is a dosage that is bioequivalent to orally administered enteric coated crofelemer at a dosage of about 250 mg per day to about 4000 mg per day. In an exemplary embodiment, crofelemer is formulated in a controlled release (delayed release) composition.

In other embodiments, the compositions of the invention can be administered in combination with analgesic or anti-inflammatory agents. In a preferred embodiment, the analgesic or anti-inflammatory agent is formulated or modified such that it is not substantially systemically absorbed, i.e., only 20%, 15%, 10%, 5%, 4%, 3%, 2%, 1% or 0.5% absorbed of the dosage given.

The present invention also provides pharmaceutical formulations of the polymeric proanthocyanidin compositions of the invention comprising the composition along with a pharmaceutically acceptable vehicle, at a dose which is therapeutically effective at treating and/or ameliorating one or more symptoms associated with c-IBS or a-IBS. In one embodiment, a directly compressible proanthocyanidin polymer composition (i.e., that can be directly compressed, without excipients, into a tablet of pharmaceutically acceptable hardness and friability) compressed into a tablet, optionally with a lubricant, such as but not limited to magnesium stearate, is enteric coated. In another embodiment, the pharmaceutical compositions of the invention alternatively include one or more substances that either neutralize stomach acid and/or enzymes or are active to prevent secretion of stomach acid. These formulations can be prepared by methods known in the art, see, e.g., methods described in *Remington's Pharmaceutical Sciences,* 18th Ed., ed. Alfonso R. Gennaro, Mack Publishing Co., Easton, Pa., 1990.

In another preferred embodiment, the pharmaceutical composition comprises a proanthocyanidin polymer composition prepared from a *Croton* spp, the dosage of which is not less than a bioequivalent dosage of orally administered enteric protected crofelemer of 250 mg per day, preferably not less than 500 mg/day. In a preferred embodiment, the proanthocyanidin polymer composition of the present invention is crofelemer (CAS 148465-45-6).

The compositions of the invention can be provided in any therapeutically acceptable pharmaceutical form. The pharmaceutical composition can be formulated for oral administration as, for example but not limited to, drug powders, crystals, granules, small particles (which include particles sized on the order of micrometers, such as microspheres and microcapsules), particles (which include particles sized on the order of millimeters), beads, microbeads, pellets, pills, microtablets, compressed tablets or tablet triturates, molded tablets or tablet triturates, and in capsules, which are either hard or soft and contain the composition as a powder, particle, bead, solution or suspension. The pharmaceutical composition can also be formulated for oral administration as a solution or suspension in an aqueous liquid, as a liquid incorporated into a gel capsule or as any other convenient formulation for administration, or for rectal administration, as a suppository, enema or other convenient form. The compositions of the invention can also be provided as a controlled release system (see, e.g., Langer, 1990, *Science* 249: 1527-1533).

The pharmaceutical formulation can also include any type of pharmaceutically acceptable excipients, additives or vehicles. For example, but not by way of limitation, diluents or fillers, such as dextrates, dicalcium phosphate, calcium sulfate, lactose, cellulose, kaolin, mannitol, sodium chloride, dry starch, sorbitol, sucrose, inositol, powdered sugar, bentonite, microcrystalline cellulose, or hydroxypropylmethylcellulose may be added to the inhibitor molecule to increase the bulk of the composition. Also, binders, such as but not limited to, starch, gelatin, sucrose, glucose, dextrose, molasses, lactose, acacia gum, sodium alginate, extract of Irish moss, panwar gum, ghatti gum, mucilage of isapgol husks, carboxymethylcellulose, methylcellulose, polyvinylpyrrolidone, Veegum and starch arabogalactan, polyethylene glycol, ethylcellulose, and waxes, may be added to the formulation to increase its cohesive qualities. Additionally, lubricants, such as but not limited to, talc, magnesium stearate, calcium stearate, stearic acid, hydrogenated vegetable oils, polyethylene glycol, sodium benzoate, sodium acetate, sodium chloride, leucine, carbowax, sodium lauryl sulfate, and magnesium lauryl sulfate may be added to the formulation. Also, glidants, such as but not limited to, colloidal silicon dioxide or talc may be added to improve the flow characteristics of a powdered formulation. Finally, disintegrants, such as but not limited to, starches, clays, celluloses, algins, gums, crosslinked polymers (e.g., croscarmelose, crospovidone, and sodium starch glycolate), Veegum, methylcellulose, agar, bentonite, cellulose and wood products, natural sponge, cation-exchange resins, alginic acid, guar gum, citrus pulp, carboxymethylcellulose, or sodium lauryl sulfate with starch may also be added to facilitate disintegration of the formulation in the intestine.

In one aspect of this embodiment, crofelemer is formulated for oral administration. In other aspects, the pharmaceutical dosage form is formulated to protect the composition, e.g., crofelemer, from degradation by the acidic conditions of the stomach and from interactions with proteins, such as pepsin, present in the stomach. Thus, in a preferred aspect, the formulation is enteric coated. For example, the enteric coated formulation is enteric coated tablets, beads or granules, which optionally contain a lubricant such as, but not limited to, magnesium stearate. The enteric coated formulations include enteric coated beads in a capsule, enteric coated microspheres in a capsule, enteric coated microspheres provided in a suspension or mixed with food, which suspensions are particularly convenient for pediatric administration, and enteric coated compressed tablets. The capsule can be a hard-shell gelatin capsule or a cellulose capsule. In particular, the pharmaceutical composition is formulated as an enteric coated capsule. In one specific aspect, a proanthocyanidin polymer composition is administered in tablet form, which tablet is backfilled with microcrystalline cellulose.

In one embodiment, the composition is directly compressed, that is, the composition of the invention, with or without any excipients, can be compressed into a tablet, or other pharmaceutical formulation, that has a pharmaceutically acceptable hardness and friability. Preferably, the directly compressible pharmaceutical composition can be compressed into tablets having a hardness of greater than 4 kp (kiloponds), preferably a hardness of 8 to 14 kp, more preferably a hardness of 10 to 13 kp. A directly compressible composition can be compressed into a tablet that has a friability of not more than 1% loss in weight, preferably less than 0.8% loss in weight, more preferably less than 0.5% loss in weight.

In a preferred embodiment, the directly compressible formulation consists of 99.93% crofelemer and 0.07% magnesium stearate and is coated with a methacrylic acid copolymer. In another preferred embodiment, the pharmaceutical formulation contains a directly compressible composition but no excipients, additives or vehicles other than an enteric coating; however, the formulation may contain a lubricant, such as but not limited to, magnesium stearate. Preferably, a directly compressed proanthocyanidin polymer composition formulation is formulated as a tablet of pharmaceutically acceptable hardness (greater than 4 kp, preferably 8-14 kp, and more preferably 10-13 kp) and friability (not more than 1% loss in weight, preferably less than 0.8% loss in weight, and more preferably less than 0.5% loss in weight).

In a more preferred embodiment, a composition of the invention is enteric coated. Enteric coatings are those coatings that remain intact in the stomach, but will dissolve and release the contents of the dosage form once it reaches the small intestine. A large number of enteric coatings are prepared with ingredients that have acidic groups such that, at the very low pH present in the stomach, i.e. pH 1.5 to 2.5, the acidic groups are not ionized and the coating remains in an undissociated, insoluble form. At higher pH levels, such as in the environment of the intestine, the enteric coating is converted to an ionized form, which can be dissolved to release the inhibitor molecule. Other enteric coatings remain intact until they are degraded by enzymes in the small intestine, and others break apart after a defined exposure to moisture, such that the coatings remain intact until after passage into the small intestines.

Polymers which are useful for the preparation of enteric coatings include, but are not limited to, shellac, starch and amylose acetate phthalates, styrene-maleic acid copolymers, cellulose acetate succinate, cellulose acetate phthalate (CAP), polyvinylacetate phthalate (PVAP), hydroxypropylmethylcellulose phthalate (grades HP-50 and HP-55), ethylcellulose, fats, butyl stearate, and methacrylic acid-methacrylic acid ester copolymers with acid ionizable groups (including "ACRYLEZE®" and "EUDRAGIT®"), such as "EUDRAGIT® L 30D", "EUDRAGIT® RL 30D", "EUDRAGIT® RS 30D", "EUDRAGIT® L 100-55", and "EUDRAGIT® L 30D-55". In a preferred embodiment, the pharmaceutical composition contains a polymeric proanthocyanidin composition and the enteric coating polymer "EUDRAGIT® L 30D", an anionic copolymer of methacrylic acid and methyl acrylate with a mean molecular weight of 250,000 Daltons. In another preferred embodiment, the enteric coating polymer is "EUDRAGIT® L 30D-55".

The disintegration of the enteric coating occurs either by hydrolysis by intestinal enzymes or by emulsification and dispersion by bile salts, depending upon the type of coating used. For example, esterases hydrolyze esterbutyl stearate to butanol and stearic acid and, as the butanol dissolves, the stearic acid flakes off of the medicament. Additionally, bile salts emulsify and disperse ethylcellulose, hydroxypropylmethylcellulose, fats and fatty derivatives. Other types of coatings are removed depending on the time of contact with moisture, for example coatings prepared from powdered carnauba wax, stearic acid, and vegetable fibers of agar and elm bark rupture after the vegetable fibers absorb moisture and swell. The time required for disintegration depends upon the thickness of the coating and the ratio of vegetable fibers to wax.

Application of the enteric coating to the polymeric proanthocyanidin composition of the invention can be accomplished by any method known in the art for applying enteric coatings. For example, but not by way of limitation, the enteric polymers can be applied using organic solvent based solutions containing from 5 to 10% w/w polymer for spray applications and up to 30% w/w polymer for pan coatings. Solvents that are commonly in use include, but are not limited to, acetone, acetone/ethyl acetate mixtures, methylene chloride/methanol mixtures, and tertiary mixtures containing these solvents. Some enteric polymers, such as methacrylic acid-methacrylic acid ester copolymers can be applied using water as a dispersant. The volatility of the solvent system must be tailored to prevent sticking due to tackiness and to prevent high porosity of the coating due to premature spray drying or precipitation of the polymer as the solvent evaporates.

Furthermore, plasticizers can be added to the enteric coating to prevent cracking of the coating film. Suitable plasticizers include the low molecular weight phthalate esters, such as diethyl phthalate, acetylated monoglycerides, triethyl citrate, polyethyl glycoltributyl citrate and triacetin. Generally, plasticizers are added at a concentration of 10% by weight of enteric coating polymer weight. Other additives such as emulsifiers, for example detergents and simethicone, and powders, for example talc, may be added to the coating to improve the strength and smoothness of the coating. Additionally, pigments may be added to the coating to add color to the pharmaceutical formulation.

In preferred embodiments, a pharmaceutical composition of the polymeric proanthocyanidin composition is provided as enteric coated beads in hard-shell gelatin capsules. In a preferred embodiment, proanthocyanidin polymer beads are prepared by mixing a proanthocyanidin polymer composition with hydroxypropylmethylcellulose and layering the mixture onto nonpareil seeds (sugar spheres). In a more preferred embodiment, crofelemer, which is directly compressible, without any excipients, additives or vehicles other than an enteric coating, is milled and fractionated into beads (i.e., as beads that do not contain the nonpareil sugar seeds). The beads may be covered with a seal coat of Opadry Clear (mixed with water). A preferred enteric coating of the beads is "EUDRAGIT™ L 30D" or "EUDRAGIT™ L 30D-55" applied as an aqueous dispersion containing 20%-30% w/w dry polymer substance, which is supplied with 0.7% sodium lauryl sulfate NF (SLS) and 2.3% polysorbate 80 NF (Tween™ 20) as emulsifiers, to which plasticizers, such as polyethylene glycol and/or citric acid esters, are added to improve the elasticity of the coating, and talc can be added to reduce the tendency of the enteric coating polymer to agglutinate during the application process and to increase the smoothness of the film coating.

In a preferred formulation, the final composition of enteric coated proanthocyanidin polymer composition beads containing the nonpareil seeds is 17.3% w/w nonpareil seeds, 64.5% w/w proanthocyanidin polymer composition, 1.5% w/w hydroxypropylmethylcellulose, 0.5% w/w Opadry clear, 14.5% w/w "EUDRAGIT™ L 30D", 1.45% w/w triethyl citrate, and 0.25% w/w glyceryl monostearate. This pharmaceutical formulation may be prepared by any method known in the art or by the method described in Example 1, infra.

A preferred formulation of the proanthocyanidin polymer composition beads not containing the nonpareil seeds is 78% w/w directly compressible proanthocyanidin polymer composition (e.g., isolated by the method described in the Examples), 0.76% w/w Opadry Clear, 19% w/w "EUDRAGIT™ L 30D-55", 1.9% triethyl citrate, and 0.34% w/w glyceryl monostearate. This pharmaceutical formulation may be prepared by any method known in the art or by the method described in Example 2, infra.

Another preferred formulation contains 54.58% w/w proanthocyanidin polymer composition beads (without nonpareil seeds and made of a directly compressible proanthocyanidin polymer composition), 1.78% w/w Opadry Clear, 39% w/w "EUDRAGIT™ L 30D-55, 3.9% triethylcitrate, and 0.74% w/w glyceryl monostearate.

In another embodiment, the pharmaceutical composition comprising the polymeric proanthocyanidin composition of the invention is formulated as enteric coated granules or powder (microspheres with a diameter of 300-500 g) provided in either hard shell gelatin capsules or suspended in an oral solution for pediatric administration. The enteric coated powder or granules may also be mixed with food, particularly for pediatric administration. This preparation may be prepared using techniques well known in the art, such as the method described in Example 1 C, infra.

In general, the granules and powder can be prepared using any method known in the art, such as but not limited to, crystallization, spray-drying or any method of comminution, preferably using a high speed mixer/granulator. Examples of high speed mixer/granulators include the "LITTLEFORD LODIGE™" mixer, the "LITTLEFORD LODIGE™" MGT mixer/granulator, and the "GRAL™" mixer/granulator. During the high-shear powder mixing, solutions of granulating agents, called binders, are sprayed onto the powder to cause the powder particles to agglomerate, thus forming larger particles or granules. Granulating agents which are useful for preparing the granules, include but are not limited to, cellulose derivatives (including carboxymethylcellulose, methylcellulose, and ethylcellulose), gelatin, glucose, polyvinylpyrrolidone (PVP), starch paste, sorbitol, sucrose, dextrose, molasses, lactose, acacia gum, sodium alginate, extract of Irish moss, panwar gum, ghatti gum, mucilage of isapol husks, Veegum and larch arabogalactan, polyethylene glycol, and waxes. Granulating agents may be added in concentrations ranging from 1 to 30% of the mass of the particles or granules.

The powder or granules are preferably coated using the fluidized bed equipment. The granules or powder may then be covered with a seal coat of Opadry Clear (mixed with water). A preferred enteric coating is "EUDRAGIT™ L 30D" applied as an aqueous dispersion containing 30% w/w dry polymer substance, which is supplied with 0.7% sodium lauryl sulfate NF (SLS) and 2.3% polysorbate 80 NF (Tween™ 20) as emulsifiers, to which the plasticizers, polyethylene glycol and citric acid esters, are added to improve the elasticity of the coating, and talc is added to reduce the tendency of the enteric coating polymer to agglutinate during the application process and to increase the smoothness of the film coating. In a preferred embodiment, the final composition of an enteric coated powder is 81.8% w/w proanthocyanidin polymer composition, 1.5% w/w hydroxypropylmethylcellulose, 0.5% w/w Opadry clear, 14.5% w/w "EUDRAGIT™ L 30D", 1.45% w/w triethyl citrate, and 0.25% w/w glyceryl monostearate. The final composition of the enteric coated granules is 81.8% w/w proanthocyanidin polymer composition, 10% polyvinylpyrrolidone, 1.5% w/w hydroxypropylmethylcellulose, 0.5% w/w Opadry clear, 14.5% w/w "EUDRAGIT™ L 30D", 1.45% w/w triethyl citrate, and 0.25% w/w glyceryl monostearate.

The enteric coated granules or powder particles can further be suspended in a solution for oral administration, particularly for pediatric administration. The suspension can be prepared from aqueous solutions to which thickeners and protective colloids are added to increase the viscosity of the solution to prevent rapid sedimentation of the coated powder particles or granules. Any material which increases the strength of the hydration layer formed around suspended particles through molecular interactions and which is pharmaceutically compatible with the inhibitor molecule can be used as a thickener, such as but not limited to, gelatin, natural gums (e.g., tragacanth, xanthan, guar, acacia, panwar, ghatti, etc.), and cellulose derivatives (e.g., sodium carboxymethylcellulose, hydroxypropylcellulose, and hydroxypropylmethylcellulose, etc.). Optionally, a surfactant such as Tween™ may be added to improve the action of the thickening agent. A preferred suspension solution is a 2% w/w hydroxypropylmethylcellulose solution in water containing 0.2% Tween™

The polymeric proantocyanidin composition can also be formulated as enteric coated tablets. In one preferred embodiment, a proanthocyanidin polymer composition is granulated with any pharmaceutically acceptable diluent (such as those listed above) by the methods described above for preparing the granules. Then, the granules are compressed into tablets using any method well known in the art, for example but not limited to, the wet granulation method, the dry granulation method or the direct compression method. Preferred diluents include, but are not limited to, microcrystalline cellulose ("AVICEL™ PH 200/300") and dextrates ("EMDEX™"). Additionally, disintegrants, such as those described above, and lubricants, such those described above, may also be added to the tablet formulation. A preferred tablet formulation contains 250 mg proanthocyanidin polymer composition, 7 mg of the disintegrant "AC-DI-SOL™" (cross linked sodium carboxymethylcellulose), 1.75 mg of the lubricant magnesium stearate and the weight of "AVICEL™ PH 200/300" necessary to bring the mixture up to 350 mg. The tablets are coated with an enteric coating mixture prepared from 250 grams "EUDRAGIT™ L 30 D-55, 7.5 grams triethyl citrate, 37.5 grains talc and 205 grams water. This formulation may be prepared by any method well known in the art.

In a preferred embodiment, a directly compressible proanthocyanidin polymer composition is made into granules by size reduction (e.g., as described above) and mixed with a lubricant, preferably, magnesium stearate. Then, the lubricated granules are compressed into tablets using any method well-known in the art, for example but not limited to, the direct compression method. Preferably, each tablet is 125 mg containing 99.6% w/w directly compressible proanthocyanidin polymer composition and 0.40% w/w magnesium stearate. The tablets are then preferably coated with an enteric coating mixture of a 30% suspension (6.66 g in 22.22 g) of "EUDRAGIT™ L 30D-55", 0.67 g triethyl citrate, 1.67 g talc and 20.44 g purified water, per 100 grams of tablet. The tablets can be prepared by any method known in the art or by the method described in Example 1E, infra.

In another embodiment, a directly compressible proanthocyanidin polymer composition is formulated into core tablets of either 125 mg, 250 mg or 500 mg containing 99.6% w/w directly compressible proanthocyanidin polymer composition and 0.40% w/w magnesium stearate. The tablets are then preferably coated with an enteric coating mixture. The final composition of the tablets is 86.6% w/w directly compressible proanthocyanidin polymer composition, 0.4% magnesium stearate, 6.5% "EUDRAGIT™ L30D-55", 0.9% triethyl citrate, 2.87% talc, and 2.74% white dispersion. The tablets can be prepared by any method known in the art, for example but not limited to the method described infra.

The compositions formed into small particles (which include particles sized on the order of micrometers, such as micro spheres and microcapsules), particles (which include particles sized on the order of millimeters), drug crystals, pellets, pills and microbeads can be coated using a fluidized-bed process. This process uses fluidized-bed equipment, such as that supplied by "GLATT™", "AEROMATIC™", "WURSTER™", or others, by which the composition cores are whirled up in a closed cylindrical vessel by a stream of air, introduced from below, and the enteric coat is formed by spray drying it onto the cores during the fluidization time. To coat tablets or capsules, Accela-Cota coating equipment ("MANESTY™") can be used. By this process, the tablets or capsules are placed in a rotating cylindrical coating pan with a perforated jacket and spraying units are installed within the pan and the dry air is drawn in through the rotating tablets or capsules. Any other type of coating pan, such as the "COMPU-LAB™" pan, Hi-coates "GLATT™" immersion sword process, the "DRIAM™" Dricoater, "STEINBERG™" equipment, "PELLEGRINI™" equipment, or "WALTHER™" equipment can also be used.

The pharmaceutical formulations of the invention can also be used to treat c-IBS in non-human animals, particularly in farm animals, such as but not limited to, bovine animals, swine, ovine animals, poultry (such as chickens), and equine animals, and other domesticated animals such as canine animals and feline animals. In particular, the pharmaceutical formulations of the invention can be used to treat c-IBS disease in non-human animals, particularly food animals such as cattle, sheep and swine by incorporating the pharmaceutical compositions of the invention into the animal's feed.

According to the methods of the present invention, the pharmaceutical compositions of comprising polymeric proanthocyanidin compositions of the invention are administered to a subject in a total amount that is bioequivalent to not less than 50 mg/day of orally administered enteric protected crofelemer. In specific embodiments, pharmaceutical compositions comprising crofelemer are administered to a subject in an amount of between about 50 mg per day and about 4000 mg/day.

In determining whether a subject has constipation-predominant IBS or alternating diarrhea/constipation predominant-IBS, any method can be used in the art to diagnose the subject including, but not limited to, the Rome II criteria for diagnosis of irritable bowel syndrome (Thompson et al., 1999, *Gut* 45 (Suppl II):I1-43-1147). Briefly, the Rome II diagnostic criteria state that for at least 12 weeks, which need not be consecutive, in the preceding 12 months of abdominal discomfort or pain that has two of three features: (1) relief with defecation, and/or (2) onset associated with a change in frequency of stool; and/or (3) onset associated with a change in form (appearance) of stool. Exemplary symptoms of c-IBS include pain; abdominal discomfort, such as abdominal fullness, bloating or swelling; abnormal stool frequency, i.e., fewer than three bowel movements per week; hard or lumpy stools; straining during a bowel movement; urgency and feeling of incomplete bowel movement. For example, abnormal stool frequency, e.g., fewer than three times a week, supports the diagnosis of c-IBS. Exemplary symptoms of a-IBS include periods of fewer than three bowel movements per week; periods of more that three bowel movements pre day; sometimes hard or lumpy stools, sometimes loose or watery stools; straining during a bowel movement; urgency; feeling of incomplete bowel movement; passing mucus during a bowel movement and abdominal fullness, bloating and swelling. Patients who switch between constipation and diarrhea have consistent abdominal pain and discomfort with both.

Definitions

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The practice of the present invention will employ, unless otherwise indicated, conventional techniques of molecular biology (including recombinant techniques), microbiology, cell biology, biochemistry, nucleic acid chemistry, and immunology, which are within the skill of the art. Such techniques are explained fully in the literature, such as, Current Protocols in Immunology (J. E. Coligan et al., eds., 1999, including supplements through 2001); Current Protocols in Molecular Biology (F. M. Ausubel et al., eds., 1987, including supplements through 2001); Molecular Cloning: A Laboratory Manual, third edition (Sambrook and Russel, 2001); PCR: The Polymerase Chain Reaction, (Mullis et al., eds., 1994); The Immunoassay Handbook (D. Wild, ed., Stockton Press NY, 1994); Bioconjugate Techniques (Greg T. Hermanson, ed., Academic Press, 1996); Methods of Immunological Analysis (R. Masseyeff, W. H. Albert, and N. A. Staines, eds., Weinheim: VCH Verlags gesellschaft mbH, 1993), Harlow and Lane Using Antibodies: A Laboratory Manual Cold Spring Harbor Laboratory Press, Cold Spring Harbor, N.Y., 1999; and Beaucage et al., eds., Current Protocols in Nucleic Acid Chemistry John Wiley & Sons, Inc., New York, 2000).

As used herein, the term "derivative" in the context of a non-proteinaceous derivative refers to a second organic or inorganic molecule that is formed based upon the structure of a first organic or inorganic molecule. A derivative of an organic molecule includes, but is not limited to, a molecule modified, e.g., by the addition or deletion of a hydroxyl, methyl, ethyl, carboxyl, amine group, esterification, alkylation or phosphorylation, immobilization or addition of a polymer.

As used herein, the term "polymer" refers to compounds comprising three or more monomeric units which may be the same or different. Thus, "polymer" refers to high molecular weight and/or insoluble polymers as well as low molecular weight and/or soluble oligomers.

As used herein, the terms "subject" and "patient" are used interchangeably. As used herein, the terms "subject" and "subjects" refer to an animal, preferably a mammal including a non-primate (e.g., a cow, pig, horse, cat, dog, rat, and mouse) and a primate (e.g., a monkey, such as a cynomolgous monkey, and a human), and more preferably a human. In a preferred embodiment, the subject is a human. In a one embodiment, the term "subject" excludes those subjects who suffer from or have been diagnosed with secretory (acute) diarrhea.

As used herein, the terms "treat", "treatment" and "treating" refer to the prevention, reduction, amelioration or elimination of a symptom or complication of c-IBS.

The term "prevention, reduction, amelioration or elimination of a symptom of c-IBS" in the context of the present invention refers to at least one of the following: prevention of c-IBS before it occurs, for example, in patients that suffered in the past from c-IBS but are now in a period of remission; elimination of established c-IBS (as determined by, for example, the return of normal stool frequency); elimination of pain associated with c-IBS; reduction of an undesired symptom of the disease as manifested by a decrease in the severity of an existing condition of c-IBS; elimination or reduction of one or more medications used in treating the subject. The reduction in the undesired symptom may be determined by, for example, measuring stool frequency, determining stool consistency, determining pain associated with c-IBS. Any amount of reduction in the severity of a symptom, even if some of the symptom remains at a lower, more acceptable level ("management"), is encompassed by the term herein defined. Such remediation may be evident as an increase in stool frequency, lessening of pain.

Since c-IBS is always accompanied by other non diarrhea-related symptoms, such as abdominal discomfort, pain, bloating, fatigue, sleep disturbances, sexual dysfunction, headache, fibromyalgia (muscle aching), dyspepsia (upper abdominal discomfort or pain), chest pain, urinary or gynecological symptoms, anxiety and depression. Reduction in at least one of these symptoms is also encompassed by the term "prevention reduction, management or elimination of a symptom or complication of c-IBS."

As used herein, the terms "treat", "treatment" and "treating" refer to the prevention, reduction, amelioration or elimination of a symptom or complication of a-IBS.

The term "prevention, reduction, amelioration or elimination of a symptom of a-IBS" in the context of the present invention refers to at least one of the following: prevention of a-IBS before it occurs, for example, in patients that suffered in the past from a-IBS but are now in a period of remission; elimination of established a-IBS (as determined by, for example, the return of normal stool frequency); elimination of pain associated with a-IBS; reduction of an undesired symptom of the disease as manifested by a decrease in the severity of an existing condition of a-IBS; elimination or reduction of one or more medications used in treating the subject. The reduction in the undesired symptom may be determined by, for example, measuring stool frequency, determining stool consistency, determining pain associated with a-IBS. Any amount of reduction in the severity of a symptom, even if some of the symptom remains at a lower, more acceptable level ("management"), is encompassed by the term herein defined. Such remediation may be evident as an increase in stool frequency, lessening of pain.

Since a-IBS is always accompanied by other non diarrhea/constipation-related symptoms, such as abdominal discomfort, pain, bloating, fatigue, sleep disturbances, sexual dysfunction, headache, fibromyalgia (muscle aching), dyspepsia (upper abdominal discomfort or pain), chest pain, urinary or gynecological symptoms, anxiety and depression. Reduction in at least one of these symptoms is also encompassed by the term "prevention reduction, management or elimination of a symptom or complication of a-IBS."

As used herein, the term "therapeutically effective amount" refers to that amount of the therapeutic agent sufficient to result in the treatment of c-IBS or a-IBS, to prevent advancement of c-IBS or a-IBS, cause regression of c-IBS or a-IBS, or to enhance or improve the therapeutic effect(s) of another therapeutic agent administered to treat or prevent c-IBS or a-IBS.

The following series of Examples are presented for purposes of illustration and not by way of limitation on the scope of the invention.

EXAMPLES

Example 1

Preparation of Pharmaceutical Formulations

Described below are illustrative methods for the manufacture and packaging for different preferred pharmaceutical formulations of the proanthocyanidin polymer composition from *C. lechleri* according to the present invention.

1A. Encapsulated Enteric Coated Beads

Detailed descriptions of the batch formula and methods used to prepare the encapsulated enteric coated proanthocyanidin polymer composition bead formulation based on sugar spheres are provided below. Each hard-shell gelatin capsule contained 250 mg proanthocyanidin polymer composition enteric coated beads. Capsules were packaged in HDPE bottles containing sixteen (16) 250 mg caps each. The formulation for enteric coated proanthocyanidin polymer composition beads contained 17.3% (w/w) of nonpareil seeds (sugar spheres 40/60 mesh, Paulaur, lot #60084060), 64.5% proanthocyanidin polymer composition from *C. lechleri*, 1.5% hydroxypropylmethylcellulose (Methocel E5 Premium, Dow Chemical Co., lot #MM9410162E), 0.5% Opadry Clear (Colorcon, lot #S83563), 14.5% "EUDRAGIT™ L 30D" (Rohm Tech., lot #1250514132), 1.45% triethyl citrate (Morflex, lot #N5X291), glyceryl monostearate (Imwitor-900, Rohm Tech, lot #502-229), and purified water (USP).

The layering coating solution containing the proanthocyanidin polymer composition was prepared by adding hydroxypropylmethylcellulose and the proanthocyanidin polymer composition to purified water (USP) and mixing until dissolved. The nonpareil seeds were loaded into the product bowl of the fluid bed processor (Nior-Precision Coater). The polymer solution was then layered on the nonpareil seeds by spraying the solution onto the fluidized nonpareil seeds at a target bed temperature of 30-35° C. Once the proanthocyanidin polymer layering had been completed, a seal coat using Opadry Clear (preparing by mixing the Opadry Clear with Purified Water, USP) was applied with a target bed temperature of 30-35° C. After the seal coat was applied, the pellets were discharged and screened through 1000μ and 425μ screens, and the layered spheres larger than 425μ and smaller than 1000μ were charged back into the fluid bed processor. Meanwhile, the enteric coating solution was prepared by mixing triethyl citrate and glyceryl monostearate to water that had been heated to 65° C. and then mixing this solution with the "EUDRAGIT™ L 30D-55". The resulting enteric coating solution was then sprayed onto the layered spheres in the fluidized bed processor, at a bed temperature of 30-35° C., until all the enteric coating solution was layered on the beads. Based on the results of the HPLC assay indicating that the proanthocyanidin polymer composition was present at a concentration of 52.9%, the enteric coated beads were hand filled into a Size #0 hard shell gelatin capsule to provide a 250 mg dosage and then packaged into a suitable HDPE bottles with a heat induction lined cap.

TABLE 1

BATCH FORMULA
Product: Proanthocyanidin Polymer Enteric Coated Beads

Batch Size: 578.0 gm

| Raw Material | Amount Used Per Batch |
|---|---|
| Sugar Nonpareil Spheres, NF (40/60) | 100.0 gm |
| Proanthocyanidin Polymer Composition | 372.8 gm |
| Hydroxypropylmethylcellulose E5, USP (K29/32) | 8.7 gm |
| Opadry Clear (YS-1-19025A) | 2.9 gm |
| "EUDRAGIT™ L 30D-55" (30% solids) | 279.4 gm |
| Triethyl Citrate, NF | 8.4 gm |
| Glycerol Monostearate | 1.4 gm |
| Water, USP (Removed during processing) | 1284.8 gm |

1B. Encapsulated Enteric Coated Beads

Described below are the formula and methods used to prepare encapsulated enteric coated bead formulations that do not contain nonpareil sugar spheres. One formulation contains 83.3% w/w proanthocyanidin polymer composition, 0.5% w/w Opadry clear, 14.5% w/w "EUDRAGIT™ L 30D-55", 1.9% w/w triethyl citrate and a 0.34% glyceryl monostearate.

The beads were first seal coated with a 5% solution of Opadry clear in a 16 liter aeromatic MP-1 fluidized bed processor with a 50 mm Wurster column. The coating parameters for the application of the seal coating were an inlet temperature of 50° C. to 60° C., an outlet temperature of 25° C. to 40° C., an air volume of 30 to 40 CMH, a spray rate of 6 to 12 grams per minute, and an air pressure of 2.5 Bar. After the seal coat was applied, the beads were discharged and screened for beads larger than 425μ and smaller than 1000μ. The beads of appropriate size were then charged back into the fluid bed processes for enteric coating. For each 1000 grams of proanthocyanidin polymer composition beads, an enteric coating suspension was prepared from 811.97 grams "EUDRAGIT™ L 30D-55", 24.36 grams triethyl citrate, 4.36 grams glyceryl monostearate and 248.55 grams purified water. This suspension was prepared by gently stirring the "EUDRAGIT™ L 30D-55" suspension continually and, in a separate container, suspending and homogenizing the triethyl citrate and talc in purified water. The triethyl citrate/talc mixture was then added to the "EUDRAGIT™ L 30D-55" suspension, and the resulting coating dispersion stirred during the spraying process to avoid settling. The beads were then coated in the fluidized bed processor under the following parameters: The inlet temperature was 42° C. to 47° C.; the outlet temperature was 28° C. to 34° C.; the air volume was 30-40 CMH; the spray rate was 6-12 grams/minute; and the air pressure was 2.5 Bars. The resulting enteric coated beads were then filled into a size #0 hard shell gelatin capsule.

1C. Enteric Coated Granules and Powder Particles

Described below is a method for formulating the proanthocyanidin polymer composition as enteric coated granules or powder (microspheres with a diameter of 300-500μ) in either hard shell gelatin capsules or suspended in an oral solution. The proanthocyanidin polymer composition powder particles are prepared by high-shear powder mixing of the proanthocyanidin polymer composition and hydroxypropylmethylcellulose in a high speed mixer/granulator. The proanthocyanidin polymer composition granules are prepared by spraying polyvinylpyrrolidone on the powder in the high speed mixer/granulator so that the powder particles agglomerate to form larger granules. Using fluidized bed equipment, the granules or powder are then covered with a seal coat of Opadry Clear (mixed with water) and then coated with the enteric coating "EUDRAGIT™ L 30D" applied as an aqueous dispersion containing 30% w/w dry methacrylate polymer substance, which is supplied with 0.7% sodium lauryl sulfate NF (SLS) and 2.3% polysorbate 80 NF (Tween™ 20) as emulsifiers, to which the plasticizers, triethyl citrate and glyceryl monostearate, are added to improve the elasticity of the coating. The final composition of the enteric coated powder is 81.8% w/w proanthocyanidin polymer composition, 1.5% w/w hydroxypropylmethylcellulose, 0.5% w/w Opadry clear, 14.5% w/w "EUDRAGIT™ L 3013", 1.45% w/w triethyl citrate, and 0.25% w/w glyceryl monostearate. The final composition of the enteric coated granules is 81.8% w/w proanthocyanidin polymer composition, 10% polyvinylpyrrolidone, 1.5% w/w hydroxypropylmethylcellulose, 0.5% w/w Opadry clear, 14.5% w/w "EUDRAGIT™ L 30D", 1.45% w/w triethyl citrate, and 0.25% w/w glyceryl monostearate.

The enteric coated proanthocyanidin polymer composition granules or particles may be filled into a hard shell gelatin capsule in an amount which provides a suitable dosage.

The enteric coated proanthocyanidin polymer composition granules or powder particles can also be suspended in a solution for oral administration, particularly for pediatric administration. The suspension solution is prepared by wetting 2 grams hydroxypropylmethylcellulose in 97.8 ml distilled water and 0.2 grams Tween™ 80; mixing this preparation to homogeneity by sonicating, heating the solution to 40° C. and stirring for three hours; and then adding the enteric coated proanthocyanidin polymer composition powder particles or granules to the homogeneous solution.

1D. Enteric Coated Compressed Tablets

A method for formulating the proanthocyanidin polymer composition with a diluent as enteric coated tablets is described below. For each 350 mg tablet, 250 mg proanthocyanidin polymer composition is granulated with 7 mg crosslinked sodium carboxymethylcellulose ("AC-DI-SOL™") and a sufficient mass of microcrystalline cellulose ("AVICEL™ PH 200/300") to bring the total mass to 350 mg. These ingredients are mixed for 20 to 30 minutes in a V blender. After the 20 to 30 minutes of mixing, 1.75 mg magnesium stearate is added and the mixture is blended for an additional 4 to 5 minutes. The resulting granules are compressed on a rotary tablet press using 5/16th inch standard concave punches. The tablets are coated with an enteric coating mixture prepared from 250 grams "EUDRAGIT™ L 30 D-55", 7.5 grams triethyl citrate, 37.5 grams talc and 205 grams water. The tablets are then placed in a perforated pan coater (e.g. the "ACCELA-COTA™" system) and rotated at 15 rpm at 40° C. The enteric coating formulation is sprayed using the following conditions: inlet air temperature of 44° C.-48° C., exhaust air temperature of 29° C.-32° C., product temperature of 26° C.-30° C., a 1 mm spray nozzle, a pan speed of 30 to 32 rpm, an airflow of 30-32 CFM, and a spray pressure of 20 PSI. The tablets are finally cured for 30 minutes as the pan is rotating at 15 rpm with an inlet air temperature of 60° C. and then, after shutting off the heat, the tablets are rotated at 15 rpm until the tablets have cooled to room temperature.

1E. Enteric Coated Directly Compressed Tablets

A method for formulating the proanthocyanidin polymer composition without a diluent as enteric coated tablets was carried out as described below. Directly compressible proanthocyanidin polymer composition was produced according to the method described in Example 1F, infra. 125 mg tablets were prepared by blending 99.6% w/w directly compressible proanthocyanidin polymer composition with 0.40% w/w magnesium stearate for two minutes and then directly compressing the material into 125 mg tablets on a rotary press using ¼ inch diameter round standard concave punches to a tablet hardness of 4-10 Kp.

The core tablets were tested and found to have an average hardness (n=10) of 4-10 Kp, friability (n=20) of less than 0.7%, an average table weight (n=10) of 125 mg±7 mg, an average thickness (n=10) of 3.9 to 4.1 mm, and a disintegration time (n=6) of not more than 20 minutes.

The coating dispersion was prepared by mixing, per 100 grams of tablets, 22.22 grams of a 30% w/w "EUDRAGIT™ L 30D-55" suspension, kept gently stirred with a mixture of 0.67 grams triethyl citrate, 1.67 grams talc and 20.44 grams purified water which had been mixed until homogeneous. The coating dispersion was continually stirred to avoid settling.

The tablets (in batches of 100,000) were coated with the coating dispersion in a Compu-Lab 24 inch/30 L pan. The tablets were jogged in the pan at a speed of 3-5 rpm and pre-warmed to a temperature of 35° C. to 40° C. The tablets were then coated with the enteric coating dispersion to a 6% to 8% weight gain with the following parameters: an inlet temperature of 45° C. to 65° C.; an exhaust air temperature of 27° C. to 34° C.; a product temperature of 28° C. to 32° C.; a pan speed of 8-14 rpm; an air flow of 180 to 240 CHM; an air spray pressure of 10-20 psi (pounds per square inch); an initial spray rate of 3 to 4 grams/min/kg; and a final spray rate of 4 to 8 grams/min/kg. The tablets were then cured for 30 minutes in the pan with an inlet temperature of 45° C. to 50° C. and a pan speed of 3 to 5 rpm. Finally, the tablets were allowed to cool to room temperature in the pan at a pan speed of 3 to 5 rpm. Four of the 125 mg tablets were then filled into a size zero, opaque Swedish orange-colored gelatin capsule.

The enteric coated proanthocyanidin polymer composition tablets were tested for content uniformity, drug release, microbiological tests and stability, and some analytical in process tests were also performed. In stability studies, the proanthocyanidin polymer composition remained stable after six months of storage at room temperature as well as under accelerated temperature and humidity conditions. Finally, the core tablets were tested and found to have an average hardness (n=10) of 4-10 Kp, friability (n=20) of less than 0.7%, an average tablet weight (n=10) of 125 mg-±7 mg, an average thickness (n=10) of 3.9 to 4.1 mm, and a disintegration time (n=6) of not more than 20 minutes.

1F. Enteric Coated Directly Compressed Tablets

Formulation of the proanthocyanidin polymer composition, without a diluent, as enteric coated tablets was carried out as described below. The directly compressible proanthocyanidin polymer composition was isolated as described in Example 2, infra. The core tablets were prepared by milling 250 mg proanthocyanidin polymer composition per tablet (approximately 16 kg total) in a Quadro Comil with an 024R (30 mesh) screen and then blending the milled composition in a Patterson Kelley 2 cubic foot twin shell blender. 1 mg magnesium stearate (Spectrum Quality Products, Inc., New Brunswick, N.J.) per tablet was then added to the composition in the blender and blended for 2 minutes. The blend was then compressed into 251 mg tablets (containing 250 mg proanthocyanidin polymer composition) on a rotary tablet press to a tablet hardness of 8-15 Kp and friability less than 0.5%.

The coating dispersion was prepared by first mixing in a first container the 25 g (7.5 g solids) "EUDRAGIT™ L 30 D-55" (Huls America, Inc., Somerset, N.J.) (weight given per 115 grams coated tablets) dispersion. The pigment dispersion was prepared by adding sequentially with constant stirring in a second container 39.59 g purified water, 3.30 grams talc (Alphafil™ 500) (Whittaker, Clark & Daniels, Inc., South Plainfield, N.J.), 6.06 g (3.15 g solids) White Dispersion (pigment) (Warner-Jenkinson, Inc., St. Louis, Mo.), and then 1.05 g triethyl citrate (Morflex, Inc., Greensboro, N.C.). The mixture was then homogenized for 15 minutes or until homogenous. While slowly stirring, the pigment dispersion was added to the "EUDRAGIT™ L 30 D-55" dispersion and then stirred for 30 minutes before spraying. Stirring was also maintained during the spraying process to avoid settling.

The tablets were coated in batches of 50,000 in a Compu-Lab 24 inch/30 L pan with the following settings: 10-20 psi atomizing air pressure; 35° C.-60° C. pan inlet air temperature; 5 to 6 inches nozzle tip to tablet bed distance; and 4/2 baffles/nozzles. After adding the tablets to the pan, the pan was jogged at a speed of 3 to 5 rpm and heated to 40° C. The tablets were then sprayed to a weight gain of 11 to 13% with the following parameters: 27°-33° C. target exhaust temperature (to be achieved within ten minutes of spraying); pan speed of 8 to 12 rpm; 180-240 CFM air flow; and a spray rate of 2-5 g/min/kg. After achieving the desired weight gain, the heat was shut off and the pan jogged at 3-5 rpm until the tablets were cooled to below 30° C.

The tablets were encapsulated in size AA opaque Swedish orange colored DB gelatin capsules (Capsugel, Greenwood, S.C.).

500 mg tablets were also produced as described above, except that coating was done on batches of 25,000 tablets to a weight gain of 8 to 10%.

Example 2

Isolation of Directly Compressible Proanthocyanidin Polymer Composition

A directly compressible proanthocyanidin polymer composition (used to prepare the formulations in Examples 1E and 1F above) was isolated from the latex of the *Croton lechleri* plant as follows:

460 liters of *Croton lechleri* latex was mixed with 940 liters purified water for ten minutes and then allowed to stand overnight (12 hours) at 4° C. The red supernatant was pumped into a holding tank and the residue discarded. The supernatant was then extracted with 200 liters n-butanol by mixing for ten minutes and then allowing the phases to separate. The n-butanol phase was discarded, and the aqueous phase was extracted two more times with 200 liters n-butanol each time. After extraction, the aqueous phase was concentrated by ultrafiltration using a 1 kD cut-off membrane (a low protein binding cellulose membrane), and then the retentate was dried in a tray dryer at approximately 37° C. (±2° C.).

For purification by column chromatography, 6 kg of the dried extract was dissolved in 75 liters of purified water and stirred for 90 minutes. The dissolved material was chromatographed on a two column chromatography system consisting of a 35 liter CM-Sepharose column (a weak cation exchange resin) and a 70 liter LH-20 column (a size-exclusion resin) connected in series. The material was loaded onto the CM-Sepharose column, washed with 140 liters purified water, and then eluted onto the LH-20 column with 375 liters of 30% acetone. At this point, the two columns were disconnected, and the proanthocyanidin polymer composition was eluted from the LH-20 column with 250 liters of 45% liters acetone. Fractions were collected into 10 liter bottles and monitored with a UV detector at 460 nm. Fractions containing material having detectable absorbance at 460 nm were pooled and concentrated by ultrafiltration using a 1 kD cut-off membrane (a low protein binding cellulose membrane). The retentate was dried using a rotary evaporator in a waterbath at approximately 37° C. (±2° C.).

The proanthocyanidin polymer composition was tested for direct compressibility. 250 mg portions of the proanthocyanidin polymer composition, in the absence of any binders or excipients, was placed into a tableting machine and then pressed into tablets of varying thicknesses (i.e., the greater the pressure on the composition to form it into a tablet, the thinner the resulting tablet). The hardness of the tablets was then determined in a conventional hardness tester. The friability of tablets having a hardness of 8-15 kp was determined as described in USP 23 <1216>. The friability was less than 0.5% loss in weight.

Example 3

Components, Composition, and Manufacturing of a Drug Product

3A. Drug Product

The drug product, crofelemer, consists of an enteric-coated 125 mg tablet(s) over-encapsulated in a Size 00, opaque Swedish orange gelatin capsule and backfilled with microcrystalline cellulose. Each capsule contains 1, 2, or 4 enteric-coated tablets. The tablet core consists of 99.93% crofelemer and 0.07% magnesium stearate and is coated with a methacrylic acid copolymer.

3B. Components of Drug Product

Crofelemer is supplied by Napo Pharmaceuticals, Inc., and is manufactured under current Good Manufacturing Practices (cGMP). Magnesium stearate is manufactured by Mallinckrodt (or equivalent) and meets the specifications for magnesium stearate as described in 27 USP/NF. The magnesium stearate is certified by the manufacturer to be derived from vegetable sources. Microcrystalline cellulose is manufactured by FMC (or equivalent) and meets the specifications for microcrystalline cellulose as described in 27 USP/NF. Both high-density and low-density microcrystalline cellulose are employed. Methacrylic acid copolymer is manufactured by DeGussa under the trade name Eudragit® (L30-D55) and meets the specifications for methacrylic acid copolymer, Type C, as described in 27 USP/NF. Triethyl citrate is manufactured by Morflex (or equivalent) and meets the specifications for triethyl citrate as described in 27 USP/NF. Talc is manufactured by Whittaker, Clark and Daniels (or equivalent) and meets the specifications for talc as described in 27 USP/NF. Purified water is supplied by the drug product manufacturer and meets the specifications for purified water as described in 27 USP/NF. Swedish orange opaque, Size 00, hard gelatin capsule bodies and caps are supplied by Capsugel, Inc. (Greenwood, S.C.). The manufacturer certifies that the capsules are made from gelatins that meet the current National Formulary (NF) requirements for gelatin under cGMP.

3C. Composition of Drug Product

The composition of the tablet cores and the enteric-coated tablets is described in Table 2 and Table 3, respectively. The amount of crofelemer and magnesium stearate is adjusted based on the anhydrous potency of the drug substance, which corrects for the moisture content of the crofelemer. The amount of weight gain after coating is approximately 10%. The clinical batch size ranges from 100,000 to 150,000 enteric-coated tablets. Subsequently, 1, 2, or 4 enteric-coated tablets are placed in a Size 00 capsule and backfilled with microcrystalline cellulose to match weights of each capsule strength and placebo.

TABLE 2

Composition of Drug Product 125 mg Tablet Cores

| Ingredient | Grade | Purpose | Quantitative Composition (w/w %) | Theoretical mg/unit dose |
|---|---|---|---|---|
| Crofelemer | cGMP | Active | 99.93% | 125 mg |
| Magnesium stearate | 27 USP/NF | Lubricant | 0.07% | 0.13 mg |
| Total | | | 100% | 125.13 mg |

TABLE 3

Composition of Drug Product Enteric-Coated 125 mg Tablets

| Ingredient | Grade | Purpose | Quantitative Composition (w/w %) | Theoretical mg/unit dose |
|---|---|---|---|---|
| Crofelemer tablet | cGMP | Active | 90.0% | 125.13 mg |
| Eudragit L-30 D55 | 27 USP/NF | Coating | 7.4% | 34.5 mg (10.4 mg solids) |
| Triethyl citrate | 27 USP/NF | Plasticizer | 0.8% | 1.05 mg |
| Talc | 27 USP/NF | Dispersing | 1.8% | 2.6 mg |
| Purified water* | 27 USP/NF | Solvent | N/A* | 21.9 mg |
| Total | | | 100% | 136.4 mg |

*Purified water is removed during process.

3D. Method of Manufacturing the Drug Product

I. Manufacture of Tablet Core

A sufficient amount of crofelemer and magnesium stearate, based on the potency of crofelemer, on an anhydrous basis that adjusts for the amount of moisture, is staged prior to manufacture. Crofelemer is added to the blender and magnesium stearate is screened and added to the crofelemer. The crofelemer and magnesium stearate are blended, a representative blend sample is taken, and the yield is determined. Yield must be between 100±3%. Blend uniformity is not determined, except as needed, because the blend is 99.9% active. The blend is directly compressed on a rotary tablet press, using ¼ inch round concave punches. Finished tablet cores are de-dusted and placed in a container to await coating. Prior to the start of the manufacturing run, pre-production runs are performed to adjust the speed and compression of the press in order to meet the targeted tablet-core weight, thickness, and hardness. In addition, friability and disintegration are measured. During the manufacturing run, tablet-core samples are taken at periodic intervals to ensure that the tablets continue to meet the targeted tablet weight, thickness, and hardness. Representative tablet cores are taken during the beginning, middle, and end of the production run for additional testing for hardness, thickness, weight, friability, and disintegration. The average tablet-core weight must be within ±5% of the targeted tablet-core weight. The number of tablet cores, sample tablet cores, tablet-core waste, and blend waste are reconciled and the percent accountability calculated. The percent accountability must not be less than 95% and not more than 103%. A schematic of the tablet core manufacturing process is presented below.

Schematic of Tablet Core Manufacturing Process

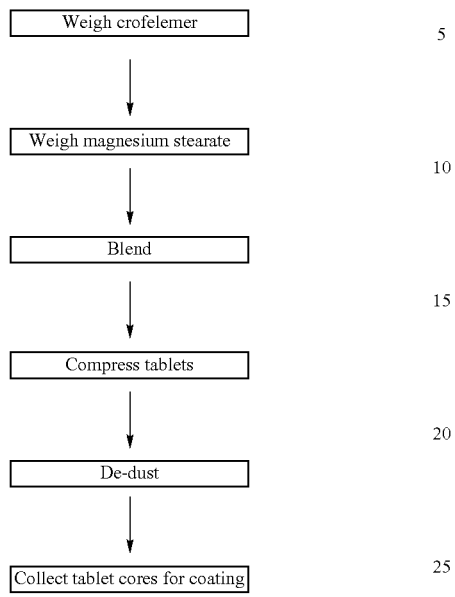

II. Coating of Tablet Core

The amount of Eudragit®, triethyl citrate, talc, and purified water is calculated and staged based on a nominal tablet-core weight gain of 10%. Purified water is charged into a suitable container equipped with a high-shear mixer. The triethyl citrate and talc are added to the container and mixed until homogenized. In a separate container equipped with a propeller mixer, the Eudragit® dispersion is charged and mixed. The triethyl citrate and talc dispersion is added to the Eudragit® dispersion and is continuously stirred throughout the spraying process. The pan-coater machine parameters are adjusted as appropriate and the lines are charged with the coating dispersion. The tablet cores are charged in a coating pan and warmed to 35 to 40° C. while jogging the coating pan. Once at temperature, the average weight of the tablet cores is recorded and the targeted coated tablet weight is calculated. Subsequently, the tablet cores are sprayed and periodically weight-checked until the targeted weight gain is met. The targeted spray rate (4 to 8 g/min/kg of tablet cores), the targeted exhaust temperature (35 to 40° C.), and inlet temperature are monitored at frequent intervals. The tablets are cured for 30 minutes at 45 to 50° C., and then cooled. Representative enteric-coated samples are taken for testing. The average enteric-coated tablet weight must be within ±5% of the targeted enteric-coated tablet weight.

The weight of enteric-coated tablets, enteric-coated tablet samples, and theoretical quantity of enteric-coated tablets are determined and the percent accountable yield calculated. The percent accountable yield must not be less than 95% and not more than 103%. The tablet-core spray-coating process is illustrated below.

Schematic of Tablet-Core Spray-Coating Process

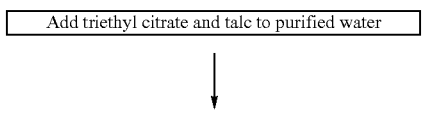

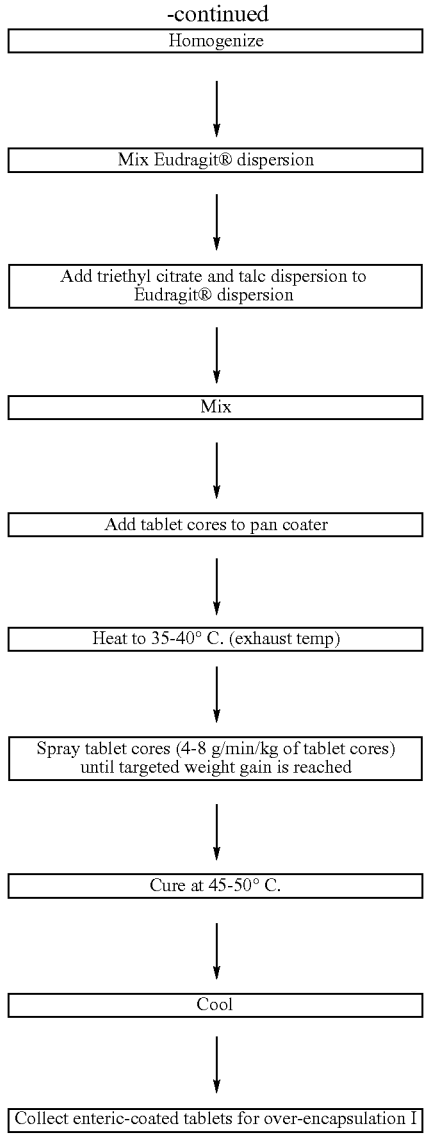

III. Manufacture of Over-Encapsulated Enteric-Coated Tablets

The enteric-coated tablets and microcrystalline cellulose are staged separately for the over-encapsulation of each capsule strength. The amount of microcrystalline cellulose to be encapsulated is calculated in order to achieve a nominal 600 to 800 mg capsule weight, dependent upon the exact dosage form (125 mg, 250 mg, or 500 mg). The average weight of the capsules is calculated based on an average of 100 capsules. The capsules are filled using a semi-automatic over-encapsulation machine fitted with Size 00 change parts and adjusted to deliver the proper amount of tablets and microcrystalline cellulose. Pre-production runs are performed in order to adjust the tray fill weight, the Add tablet cores to pan coater number of turns on the tamper, and the number of times tamped in order to meet the targeted gross capsule weight (capsule shell plus tablets and microcrystalline cellulose). Each tray is prepared by placing the capsule bodies in the capsule tray. Each capsule body is filled with the targeted amount of tablets and microcrystalline cellulose to achieve the targeted fill. The caps are placed on the bodies and closed.

The capsules are removed from the tray and de-dusted. A composite of capsules from each tray is collected and weighed for in-process and release testing. The average capsule weight is within ±5% of the targeted capsule weight. The process is then repeated until the desired number of capsules is filled. Damaged capsules, enteric-coated tablet waste, and microcrystalline cellulose waste are collected for final product reconciliation. A composite of the finished capsules is sent for release testing. The number of finished capsules, sample capsules, damaged capsules, and drug substance waste are reconciled and the percent accountability is calculated. The percent accountability must not be less than 95% and not more than 103%. A schematic of the over-encapsulation of the enteric-coated tablets is presented below.

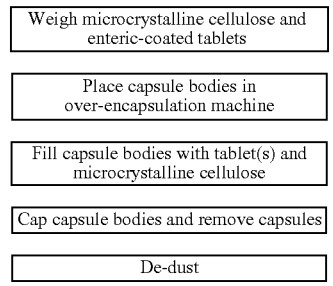

Schematic of Over-Encapsulation of Enteric-Coated Tablets

Weigh microcrystalline cellulose and enteric-coated tablets

Place capsule bodies in over-encapsulation machine

Fill capsule bodies with tablet(s) and microcrystalline cellulose

Cap capsule bodies and remove capsules

De-dust

Example 4

Effect of Enterically Coated Proanthocyanidin Polymer Composition on Patients Suffering From Diarrhea Predominant Irritable Bowel Syndrome 4A. Treatment The study was a 16-week, multi-center, Phase 2, randomized, double-blind, placebo controlled study in subjects with diarrhea predominant irritable bowel syndrome (d-IBS). Two-hundred and forty-six (246) subjects, meeting the definition of d-IBS as supported by the Rome 11 Criteria for the Diagnosis of IBS were randomized into four groups: placebo, 125 mg bid, 250 mg bid, and 500 mg bid. The study consisted of a 2-week Determine average weight of capsules treatment-free screening period, a 12-week blinded treatment period, followed by a 2-week treatment-free follow-up period.

During the 2-week screening period, subjects self-reported daily information about the status of their d-IBS symptoms via a touch-tone telephone diary. This included information about abdominal pain and discomfort, stool frequency, consistency and urgency. If the subject continued to meet the inclusion criteria at the end of the screening period, and the information captured in the diary during the screening period indicated they had active d-IBS [mean daily stool frequency≧2; pain score≧1; stool consistency≧3 (5-point Lickert scale for pain and consistency)], subjects were randomized into one of four groups according to a computer-generated central randomization schema.

During the 12-week double-blind treatment period, subjects continued to record daily and weekly assessments via a touch-tone telephone diary system as instructed. Subjects were seen every 4 weeks during the treatment period for study assessment visits at which time they received additional study medication.

During the 2-week treatment-free follow-up period, subjects continued to record daily and weekly assessments.

Results:

There were no drug-related serious adverse events. Adverse event rates were similar across all dose groups as shown in Table 4. There were no drug- or dose-related differences in constipation.

TABLE 4

Summary of Adverse Events[1]

| | Placebo | 125 mg bid | 250 mg bid | 500 mg bid |
|---|---|---|---|---|
| No. Subjects/Group | 61 | 62 | 59 | 62 |
| No. Subjects with ≧1 AE | 14 | 12 | 15 | 15 |
| No of GI AEs | 7 | 10 | 10 | 10 |
| GI Event | | | | |
| Abdominal distention | 0 | 1 | 0 | 1 |
| Abdominal pain | 1 | 2 | 1 | 2 |
| Abdominal tenderness | 0 | 0 | 1 | 0 |
| Constipation | 1 | 3 | 2 | 1 |
| Diarrhea | 1 | 2 | 1 | 0 |
| Dry mouth | 0 | 0 | 0 | 2 |
| Eructation | 0 | 0 | 0 | 1 |
| Flatulence | 1 | 1 | 3 | 1 |
| Haematochezia | 0 | 0 | 1 | 0 |
| Hemorrhoids | 0 | 1 | 0 | 0 |
| Nausea | 3 | 0 | 1 | 1 |
| Urgency | 0 | 0 | 0 | 1 |
| No. of Other AEs | 11 | 12 | 15 | 14 |
| Other Events (>1 AE/group) | | | | |
| Dizziness | 1 | 0 | 3 | 0 |
| Headache | 2 | 2 | 1 | 3 |
| Anxiety | 2 | 0 | 0 | 1 |
| Insomnia | 0 | 0 | 2 | 1 |
| Rash | 1 | 2 | 0 | 0 |

[1]possible, probably, or likely related.

In general, crofelemer 125 mg bid, as shown in Table 5 exhibited a consistent response among most efficacy endpoints in females. There appeared to be little efficacy in males; however, group size was too small (13-16/group) to analyze separately. Since crofelemer produced no constipation, stool consistency scores approached normal and were not different from placebo. In all other endpoints (frequency, urgency, adequate relief, and pain), there was an improvement in activity with each successive month and during the 2 week treatment-free follow-up period symptoms began approaching baseline levels as expected. Crofelemer 500 mg bid also had a statistically significant effect on pain (0.48 decrease in pain score; 22.44% increase in pain free days). There were 5 female disease outliers (they had >9 stools/day at baseline and were >3 standard deviations from the mean stool frequency of all randomized female subjects) that were not representative of the d-IBS population used in this study and were removed from all analyses presented in this summary.

As shown in Table 6, crofelemer at 250 mg and 500 mg bid had less of an effect on frequency and consistency than the placebo group. Subjects treated with crofelemer 500 mg bid had a greater than half of stool per day mean increase in stool frequency as compared to placebo; there mean stool consistency was 0.22 points higher (closer to loose consistency) as compared to placebo.

TABLE 5

Efficacy of Crofelemer 125 mg bid in Females

| Endpoint (Δ from Placebo) | Results[1] |
|---|---|
| Consistency Score | −0.03 |
| Frequency (stools/day) | −0.7 |
| Urgency Free Days | 11.2% |
| Pain score | −0.42* |
| Pain Free Days | 12.76%* |
| Adequate Relief | 16% |

[1]Month 3 results; observed case analysis with disease outliers (mean baseline frequency >9 stools/day) removed from all groups. 'statistically significant at $p < 0.05$

TABLE 6

The Effects of Crofelemer.250 and 500 mg bid on stool consistency and frequency

| Endpoint (Δ from Placebo) | 250 mg bid[1] | 500 mg bid[1] |
|---|---|---|
| Consistency Score | 0.19 | 0.22 |
| Frequency (stools/day) | 0.24 | 0.60 |

[1]Month 3 results: observed case analysis with disease outliers (mean 1 > 9 stools/day) removed from all groups.

Figure 4:
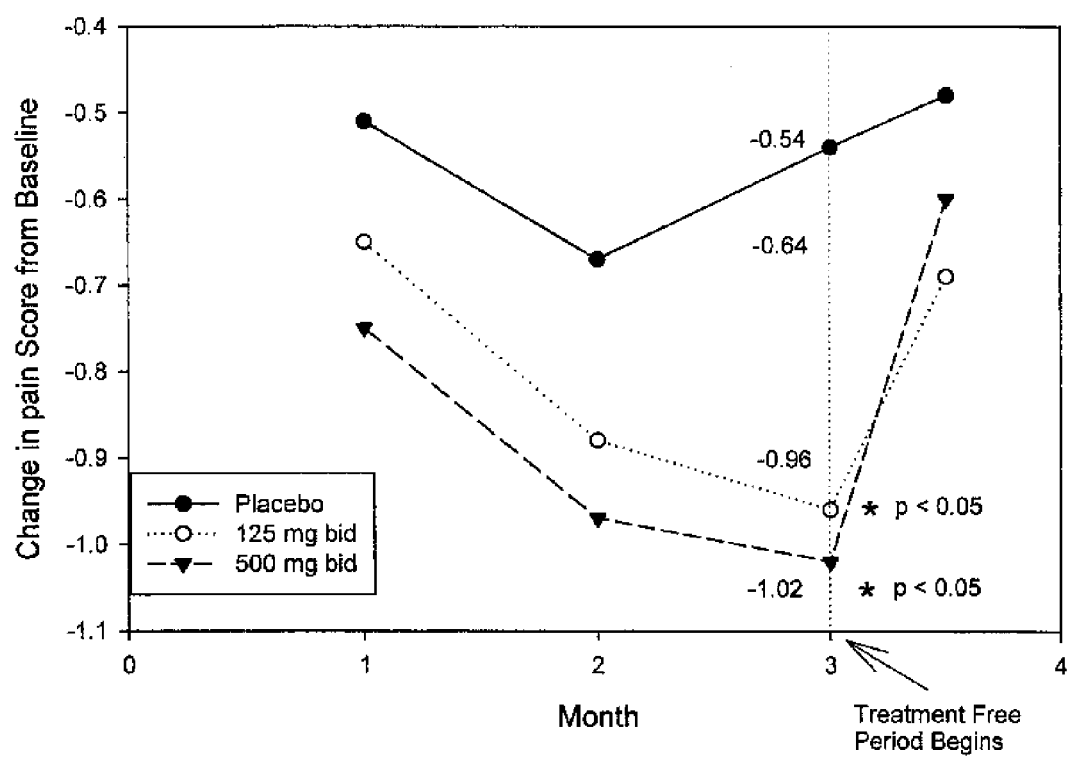
FIG. 4 is a graph illustrating the Effect of Crofelemer on Pain Score in Females.

As seen in FIG. 4, female subjects treated with crofelemer 125 mg bid had a clinically significant decrease in stool frequency. Use of crofelemer led to a decrease of greater than one bowel movement per day. The month-to-month improvement in stool frequency was contrasted by the placebo effect diminishing at month two as values began to approach baseline. When the treatment-free period began at the end of month three, the subjects stopped taking crofelemer and the effect began to go away as expected.

Figure 5:
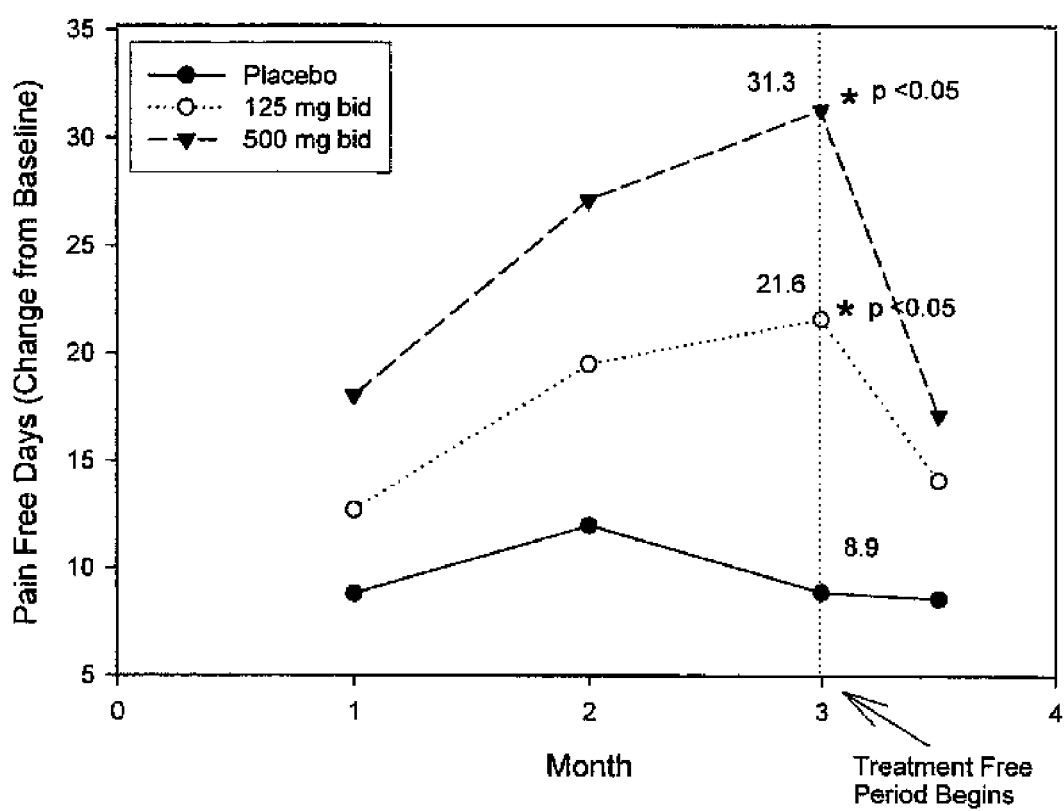
FIG. 5 is a graph illustrating the Effect of Crofelemer on Percent of Pain Free Days in Females.

As seen in FIG. 5, crofelemer produced an increase in urgency free days. At Month 3, there was a 35.1% increase in urgency free days in the crofelemer group versus a 23.9% increase in urgency free days observed in the placebo group. There was a month-to-month improvement, as commonly seen. The placebo effect peaked at month two and abruptly decreased as values begin to approach baseline. When the treatment-free period began at the end of month three, the subjects stopped taking crofelemer and the effect began to go away as expected.

Figure 6:
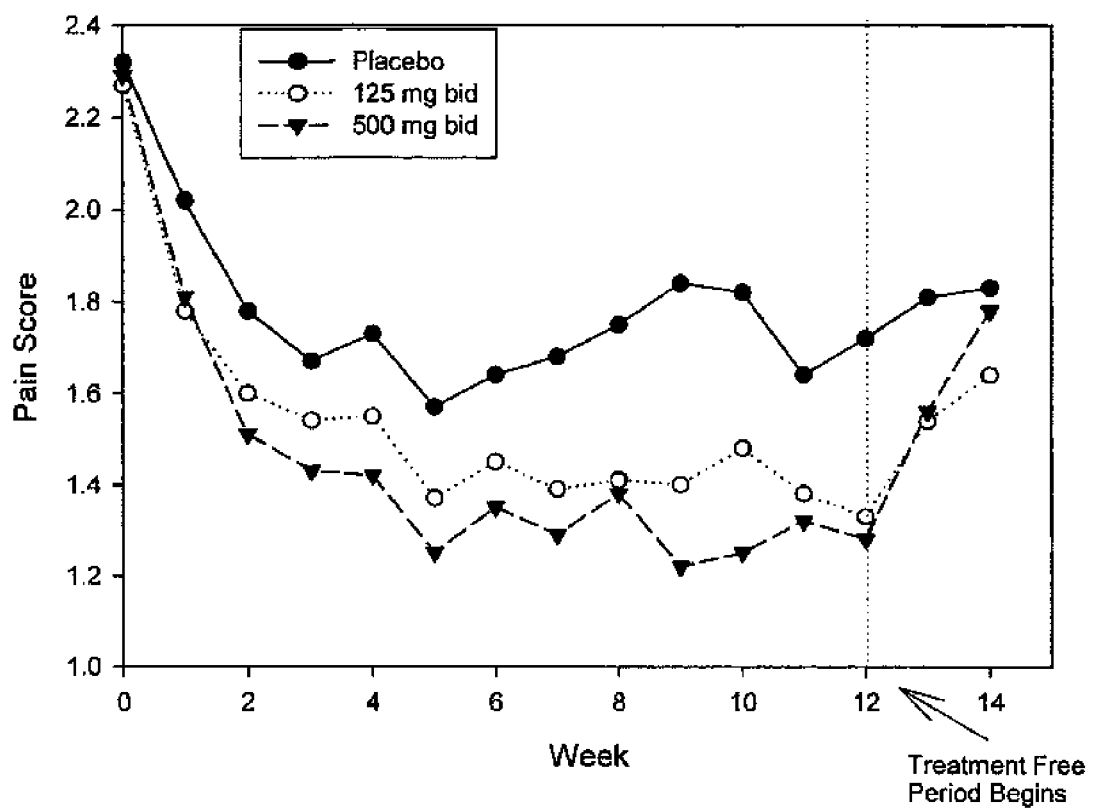
FIG. 6 is a graph illustrating the Effect of Crofelemer on Pain Score in Females.

As seen in FIG. 6, administration of crofelemer produced an increase in the percentage of subjects reporting adequate relief of d-IBS symptoms. Since d-IBS is comprised of a group of symptoms, the adequate relief endpoint is an overall assessment by the patient as to how well the treatment is addressing their d-IBS symptoms. Crofelemer at 125 mg bid caused a 16% increase in the adequate relief of d-IBS symptoms as compared to the placebo group. With the observed analysis, there was a month-to-month improvement in activity of crofelemer, i.e., the longer the patient took crofelemer, the greater relief of symptoms. As previously seen with other endpoints, the placebo effect peaked at month two and decreased thereafter.

Diarrhea-predominant IBS is differentiated from many functional bowel diseases by the close association of pain with changes in bowel habits. As defined by the Rome II Criteria for the Diagnosis of IBS, pain must be associated with abnormal bowel habits and the improvement of the bowel habits should be associated with the improvement of pain. In this study we have measured pain score with a 5-point scale, where 0 is none and 5 is severe; and the presence of pain free days. As shown in FIG. 4 and FIG. 5, female subjects treated with crofelemer (125 and 500 mg bid) had clinically and statistically significant ($p<0.05$) decreases in both pain score and pain free days. The effect is quite consistent as observed in the weekly pain score results shown in FIG. 6. This effect on pain relief was unexpected and surprising.

In conclusion, crofelemer at 125 mg bid, was safe and its administration resulted in improvement in the efficacy endpoints of pain, adequate relief, frequency, and urgency in female subjects. Crofelemer at 250 and 500 mg bid was safe and, compared to placebo, appeared to worsen the diarrheal symptoms of consistency and frequency. Crofelemer at 125 and 500 mg bid produced a statistically significant decrease in both pain score and pain free days in female subjects with d-IBS.

Example 5

Investigation of Crofelemer Mechanism of Action

To further investigate the mechanism of action of crofelemer, crofelemer at 10 and 100 μg/mL was evaluated in a selected panel of cellular cytokine release assays (IL-1α; TNF-α-induced and IL-1-induced PGE2 release; IFN-γ; IL-2, IL-4; IL-5; IL-6; IL-8; IL-10 and TNF-α) and molecular assays (COX-1 and COX-2 enzyme assays, and glucocorticoid, serotonin 5HT3, δ-opiod, κ-opiond, μ-opiod, and non-selective opiod receptor binding assays. Crofelemer was also tested in cytotoxicity assays corresponding to the ConA- and LPS-induced cytokine release assays as well as those corresponding to the TNF-a- and IL-1-induced PGE release assays.

At both 10 and 100 μg/mL, crofelemer caused a 73% and 100% inhibition in the COX1 and COX2 enzyme assays, respectively.

Further, crofelemer exhibited significant (>50%) inhibition in the IFN-γ; IL-2, IL-4; IL-6; IL-8; IL-10 and TNF-a cytokine release assays as well as in the TNF-α-induced and IL-1-induced PGE2 release assays at 10 and 100 μg/mL (i.e., all cytokine release assays with the exception of IL-5). Crofelemer also displayed significant cytotoxic activity in the ConA and IL-1-induced PGE2 cytotoxicity assays suggesting that in the ConA-mediated cytokine release assays (IFN-γ, IL-2, IL-4 and IL-10) and the IL-I-induced PGE2 release assay may be due to general cytotoxicity.

Example 6

Animal Toxicity Study

In an animal toxicity study, crofelemer was demonstrated to produce diarrhea in dogs at dosages of 175 mg/kg/day and 600 mg/kg/day.

In a separate example, diarrhea was induced in healthy human volunteers in a phase I study at a dosage of 2000 mg/day.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled. Such modifications are intended to fall within the scope of the appended claims.

All references, patent and non-patent, cited herein are incorporated herein by reference in their entireties and for all purposes to the same extent as if each individual publication or patent or patent application was specifically and individually indicated to be incorporated by reference in its entirety for all purposes.

What is claimed is:

1. A method of treating constipation-predominant irritable bowel syndrome (c-IBS) comprising administering to a patient in need of such treatment an effective amount of isolated crofelemer or a composition comprising isolated crofelemer as a c-IBS-treating active agent and a pharmaceutically acceptable vehicle.

2. The method of claim 1, wherein the composition orally administered in a dose of about 250 mg per day to about 4000 mg per day.

3. The method of claim 1, wherein the treatment comprises reducing one or more symptoms of c-IBS.

4. The method of claim 3, wherein the treatment comprises reducing pain or abdominal discomfort.

5. The method of claim 4, wherein pain or discomfort is reduced by at least 10%.

6. The method of claim 3, wherein the treatment comprises reducing constipation or less than normal stool frequency.

7. The method of claim 6, wherein stool frequency is increased by at least one additional bowel movement per week.

* * * * *